United States Patent
Bachlava et al.

(10) Patent No.: US 10,470,385 B2
(45) Date of Patent: *Nov. 12, 2019

(54) METHODS AND COMPOSITIONS FOR PRODUCING WATERMELON PLANTS WITH SELECTED SEED SIZES

(71) Applicant: Seminis Vegetable Seeds, Inc., St. Louis, MO (US)

(72) Inventors: Eleni Bachlava, Vallejo, CA (US); Hussein Abdel-Haleem, Athens, GA (US); Steven Knapp, Woodland, CA (US); Cecilia McGregor, Athens, GA (US); Jason Prothro, Thomasville, GA (US); Katherine Sandlin, Athens, GA (US); Gregory E. Tolla, Woodland, CA (US); Victoria Brookins, Sacramento, CA (US)

(73) Assignee: SEMINIS VEGETABLE SEEDS, INC., St. Louis, MO (US)

( * ) Notice: Subject to any disclaimer, the term of this patent is extended or adjusted under 35 U.S.C. 154(b) by 1072 days.

This patent is subject to a terminal disclaimer.

(21) Appl. No.: 13/960,545

(22) Filed: Aug. 6, 2013

(65) Prior Publication Data

US 2014/0041078 A1  Feb. 6, 2014

Related U.S. Application Data

(60) Provisional application No. 61/680,232, filed on Aug. 6, 2012.

(51) Int. Cl.
*A01H 5/08* (2018.01)
*C12Q 1/6895* (2018.01)
*A01H 1/04* (2006.01)

(52) U.S. Cl.
CPC ............... *A01H 5/08* (2013.01); *A01H 1/04* (2013.01); *C12Q 1/6895* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,399,855 | B1 | 6/2002 | Beavis |
| 2005/0015827 | A1 | 1/2005 | Podlich et al. |
| 2006/0005284 | A1 | 1/2006 | Tolla et al. |
| 2009/0031438 | A1 | 1/2009 | Kennard et al. |
| 2009/0191541 | A1 | 7/2009 | Byrum |
| 2010/0306883 | A1 | 12/2010 | Tolla et al. |
| 2013/0055466 | A1 | 2/2013 | Juarez et al. |
| 2013/0298278 | A1 | 11/2013 | Bachlava et al. |
| 2014/0157450 | A1* | 6/2014 | Abdel-Haleem ........ A01H 5/08 800/260 |

FOREIGN PATENT DOCUMENTS

WO   WO 2012/069539   5/2012

OTHER PUBLICATIONS

Prothro (Genetic mapping of phenotypic and quantitative trait loci underlying horticulturally important traits in watermelon, Thesis, University of Georgia, Dec. 2010).*
Sandlin (Genetic Mapping in Citrullus lanatus, Thesis, University of Georgia, Dec. 2010).*
Sandlin (Genetic Mapping in Citrullus lanatus, Thesis, University of Georgia, Dec. 2010) (Year: 2010).*
Mauricio, R. Mapping quantitative trait loci in plants: uses and caveats for evolutionary biology. Nature Reviews Genetics 2, 370-381 (2001) (Year: 2001).*
Prothro (Genetic mapping of phenotypic and quantitative trait loci underlying horticulturally important traits in watermelon, Thesis, University of Georgia, Dec. 2010) (Year: 2010).*
Collard et al., "Marker-assisted selection: an approach for precision plant breeding in the twenty-first century," *Philosophical Transactions of the Royal Society B: Biological Sciences* 363:557-572, 2007.
Devicente et al., "QTL analysis of transgressive segregation in an interspecific tomato cross," *Genetics* 134:585-596, 1993.
Doerge et al., "Permutation tests for multiple loci affecting a quantitative character," *Genet. Mol. Biol.* 142:285-294, 1996.
Gonzalez-Ibeas et al., "Melogen: an EST database for melon functional genomics," *BioMed Central Genomics* 8(306):1-17, 2007.
Gusmini *Inheritance of fruit characteristics and disease resistance in watermelon [Citrullus lanatus (Thunb.) Matsum. & Nakai]*. Ph.D. dissertation, North Carolina State University, Raleigh, North Carolina, 2005.
Hawkins et al., "Molecular markers associated with morphological traits in watermelon," *HortScience* 36:1318-1322, 2001.
Hawkins et al., "Linkage mapping in a watermelon population segregating for *Fusarium* wilt resistance," *J. Am. Soc. Horticultural Sci.* 126(3):344-350, 2001.
Klimenko et al., "Mapping candidate QTLs related to plant persistency in red clover," *Theor. Appl. Genet.* 120:1253-1263, 2010.
Konsler et al., "The inheritance of seed size in watermelon," *American Society for Horticultural Science* 71:480-484, 1958.
Levi et al., "A genetic linkage map for watermelon derived from a testcross population: (*Citrullus lanatus* var. *citroides* x *C. lanatus* var. *lanatus*) x *Citrullus colocynthis*," *Theor. Appl. Genet.* 105(4):555-563, 2002.
Levi et al., "Genetic diversity among watermelon (*Citrullus lanatus* and *Citrullus colocynthis*) accessions," *Genet. Resour. Crop Evol.* 48:559-566, 2001a.

(Continued)

*Primary Examiner* — Lee A Visone
(74) *Attorney, Agent, or Firm* — Dentons US LLP; Alissa Eagle, Esq.

(57) ABSTRACT

The present disclosure provides for unique watermelon plants with a desired seed size phenotype and their progeny. Such plants may comprise an introgressed QTL associated with a desired seed size phenotype. In certain aspects, compositions, including distinct polymorphic molecular markers, and methods for producing, breeding, identifying, selecting, and the like of plants or germplasm with a desired seed size phenotype are provided.

18 Claims, 6 Drawing Sheets

Specification includes a Sequence Listing.

(56) References Cited

OTHER PUBLICATIONS

Levi et al., "ISSR and AFLP markers differ among American watermelon cultivars with limited genetic diversity," *J. Am. Soc. Hort. Sci.* 129:553-558, 2004.

Levi et al., "Low genetic diversity indicates the need to broaden the genetic base of cultivated watermelon," *HortScience* 36:1096-1101, 2001b.

Lou, "Inheritance of Fruit Characteristics in Watermelon [*Citrullus lanatus* (Thunb.) Matsum.& Nakai]," M.S. thesis, North Carolina State University, Raleigh, North Carolina, 2009.

Poole et al., "Inheritance of seed characters in watermelon," *J. Agr. Res.* 63:433-456, 1941.

Protho, "Genetic mapping of phenotypic and quantitative trait loci underlying horticulturally important traits in watermelon," M.S. thesis, University of Georgia, Athens, Georgia, 2010.

Protho et al., "Main and epistatic quantitative trait loci associated with seed size in watermelon," *J. Amer. Soc. Hort. Sci.* 137(6): 452-457. 2012.

Ravi et al., "Identification of several small main-effect QTLs and a large number of epistatic QTLs for drought tolerance related traits in groundnut (*Arachis hypogaea* L.)," *Theor. Appl. Genet.* 122:1119-1132, 2011.

Sandlin et al., "Comparative mapping in watermelon [*Citrullus lanatus* (Thunb.) Matsum. et Nakai]," *Theor. Appl. Genet.* 125(8):1603-1618, 2012.

Sandlin, "Genetic Mapping in *Citrullus lanatus*," M.S. thesis, University of Georgia, Athens, Georgia, 2010.

Shimotsuma et al., "Cytogenetical studies in the genus Citrullus. VII. Inheritance of several characters in watermelons," *Jap. J. Breeding* 13:235-240, 1963.

Tanaka et al., "Inheritance of fruit shape and seed size of watermelon," *J. Japan. Soc. HortScience* 64:543-548, 1995.

Wehner et al., "Breeding and seed production." in: Maynard, D. N. (ed.), *Watermelons: Characteristics, Production, and Marketing* (Alexandria, VA, ASHS Press), pp. 27-73, 2001.

Zeng, "Theoretical basis of separation of multiple linked gene effects on mapping quantitative trait loci," *Proceedings of the National Academy of Sciences USA* 90:10972-10976, 1993.

Zhang et al., "Genes controlling watermelon seed size." In: Lester, G. and Dunlap, J. (eds.), *Cucurbitaceae '94: Evaluation and Enhancement of Cucurbit Germplasm.* (Alexandria, VA, ASHS Press), pp. 144-147, 1995.

Zhang, "Breeding and production of watermelon for edible seed in China," *Cucurbit Genetics Cooperative Report* 19:66-67, 1996 (http://cuke.hort.ncsu.edu/cgc/cgc19/cgc19-24.html).

Zhang et al., "Inheritance of seed size from diverse crosses in watermelon," *Cucurbit Genetics Cooperative Report* 19:67-69, 1996 (http://cuke.hort.ncsu.edu/cgc/cgc19/cgc19-25.html).

Prothro, 2010, Genetic Mapping of phenotypic and quantitative trait loci underlying horticulturally important traits in watermelon, Master of Science thesis, Athens, Georgia.†

Prothro 2010 figures of linkage groups compared to patent fig3.†

Sandlin, 2010, Genetic Mapping in Citrullus lanatus, Master of Science, Athens Goergia.†

\* cited by examiner
† cited by third party

METHODS AND COMPOSITIONS FOR PRODUCING WATERMELON PLANTS WITH SELECTED SEED SIZES

CROSS-REFERENCE TO RELATED APPLICATIONS

This applications claims the benefit of priority of U.S. Provisional Application Ser. No. 61/680,232, filed on Aug. 6, 2012, the disclosure of which is incorporated herein by reference in its entirety.

FIELD OF THE INVENTION

The present invention relates to the field of plant breeding and, more specifically, to methods and compositions for producing melon plants with desired seed size phenotypes.

INCORPORATION OF SEQUENCE LISTING

The sequence listing that is contained in the file named "SEMB007US-ST25.txt", which is 9 kilobytes as measured in Microsoft Windows operating system and was created on Aug. 6, 2013, is filed electronically herewith and incorporated herein by reference.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Advances in molecular genetics have made it possible to select plants based on genetic markers linked to traits of interest, a process called marker assisted selection (MAS). While breeding efforts to date have provided a number of useful watermelon lines and varieties with beneficial traits, there remains a need in the art for new lines and varieties with further improved traits and methods for their production. In many cases, such efforts have been hampered by difficulties in identifying and using alleles conferring beneficial traits. These efforts can be confounded by the lack of definitive phenotypic assays, and other issues such as epistasis, and polygenic or quantitative inheritance. In the absence of molecular tools such as MAS, it may not be practical to produce certain new genotypes of crop plants due to such challenges.

SUMMARY OF THE INVENTION

The invention provides, in one aspect, a watermelon plant comprising in its genome at least one introgressed allele locus associated with a desired seed size phenotype. In one embodiment, such a locus is in a genomic region defined as flanked by loci NW0248118 (SEQ ID NO: 1) and NW0248583 (SEQ ID NO: 4) on linkage group 2 (LG2), or within 15 cM thereof; loci NW0251236 (SEQ ID NO: 2) and NW0250242 (SEQ ID NO: 3) on linkage group 2 (LG2), or within 15 cM thereof; loci NW0251455 (SEQ ID NO: 5) and NW0248118 (SEQ ID NO: 1) on linkage group 2 (LG2), or within 15 cM thereof; loci NW0249249 (SEQ ID NO: 9) and NW0249873 (SEQ ID NO: 11) on linkage group 4 (LG4), or within 15 cM thereof; loci NW0250227 (SEQ ID NO: 12) and NW0249974 (SEQ ID NO: 18) on linkage group 9 (LG9), or within 15 cM thereof; or loci NW0248282 (SEQ ID NO: 19) and NW0250036 (SEQ ID NO: 22) on linkage group 11 (LG11), or within 15 cM thereof; or a progeny plant therefrom.

In certain embodiments, a desired seed size phenotype comprises one or more seed traits selected from the group consisting of an average 100 seed weight; an average seed length; and an average seed width. In further embodiments, wherein the desired seed size phenotype comprises an average 100 seed weight; an average seed length; and an average seed width.

In still further embodiments, a locus conferring a desired seed size phenotype is defined as in a genomic region flanked by: loci NW0251455 (SEQ ID NO: 5) and NW0249783 (SEQ ID NO: 6) on LG2; loci NW0249783 (SEQ ID NO: 6) and NW0250500 (SEQ ID NO: 7) on LG2; loci NW0250500 (SEQ ID NO: 7) and NW0250854 (SEQ ID NO: 8) on LG2; loci NW0250854 (SEQ ID NO: 8) and NW0248118 (SEQ ID NO: 1) on LG2; loci NW0248118 (SEQ ID NO: 1) and NW0251236 (SEQ ID NO: 2) on LG2; loci NW0248118 (SEQ ID NO: 1) and NW0250242 (SEQ ID NO: 3) on LG2; loci NW0248118 (SEQ ID NO: 1) and NW0248583 (SEQ ID NO: 4) on LG2; loci NW0251236 (SEQ ID NO: 2) and NW0250242 (SEQ ID NO: 3) on LG2; loci NW0251236 (SEQ ID NO: 2) and NW0248583 (SEQ ID NO: 4) on LG2; loci NW0250242 (SEQ ID NO: 3) and NW0248583 (SEQ ID NO: 4) on LG2; loci NW0249249 (SEQ ID NO: 9) and NW0250697 (SEQ ID NO: 10) on LG4; loci NW0249249 (SEQ ID NO: 9) and NW0249873 (SEQ ID NO: 11) on LG4; loci NW0250697 (SEQ ID NO: 10) and NW0249873 (SEQ ID NO: 11) on LG4; loci NW0250227 (SEQ ID NO: 12) and NW0250857 (SEQ ID NO: 13) on LG9; loci NW0250227 (SEQ ID NO: 12) and NW0249185 (SEQ ID NO: 14) on LG9; loci NW0250227 (SEQ ID NO: 12) and NW0249226 (SEQ ID NO: 15) on LG9; loci NW0250227 (SEQ ID NO: 12) and NW0248254 (SEQ ID NO: 16) on LG9; loci NW0250227 (SEQ ID NO: 12) and NW0249883 (SEQ ID NO: 17) on LG9; loci NW0250227 (SEQ ID NO: 12) and NW0249974 (SEQ ID NO: 18) on LG9; loci NW0250857 (SEQ ID NO: 13) and NW0249185 (SEQ ID NO: 14) on LG9; loci NW0250857 (SEQ ID NO: 13) and NW0249226 (SEQ ID NO: 15) on LG9; loci NW0250857 (SEQ ID NO: 13) and NW0248254 (SEQ ID NO: 16) on LG9; loci NW0250857 (SEQ ID NO: 13) and NW0249883 (SEQ ID NO: 17) on LG9; loci NW0250857 (SEQ ID NO: 13) and NW0249974 (SEQ ID NO: 18) on LG9; loci NW0249185 (SEQ ID NO: 14) and NW0249226 (SEQ ID NO: 15) on LG9; loci NW0249185 (SEQ ID NO: 14) and NW0248254 (SEQ ID NO: 16) on LG9; loci NW0249185 (SEQ ID NO: 14) and NW0249883 (SEQ ID NO: 17) on LG9; loci NW0249185 (SEQ ID NO: 14) and NW0249974 (SEQ ID NO: 18) on LG9; loci NW0249226 (SEQ ID NO: 15) and NW0248254 (SEQ ID NO: 16) on LG9; loci NW0249226 (SEQ ID NO: 15) and NW0248254 (SEQ ID NO: 16) on LG9; loci NW0248254 (SEQ ID NO: 16) and NW0249883 (SEQ ID NO: 17) on LG9; loci NW0248254 (SEQ ID NO: 16) and NW0249974 (SEQ ID NO: 18) on LG9; loci NW0249883 (SEQ ID NO: 17) and NW0249974 (SEQ ID NO: 18) on LG9; loci NW0248282 (SEQ ID NO: 19) and NW0249891 (SEQ ID NO: 20) on LG11; loci NW0248282 (SEQ ID NO: 19) and NW0251129 (SEQ ID NO: 21) on LG11; loci NW0248282

(SEQ ID NO: 19) and NW0250036 (SEQ ID NO: 22) on LG11; loci NW0249891 (SEQ ID NO: 20) and NW0251129 (SEQ ID NO: 21) on LG11; loci NW0249891 (SEQ ID NO: 20) and NW0250036 (SEQ ID NO: 22) on LG11; or loci NW0251129 (SEQ ID NO: 21) and NW0250036 (SEQ ID NO: 22) on LG11; or within 15 cM thereof.

In another aspect, the invention provides a method of detecting in at least one watermelon plant a genotype associated with a desired seed size phenotype. In one embodiment, the method comprises the step of: (i) detecting in at least one watermelon plant an allele of at least one polymorphic nucleic acid that is associated with a desired seed size phenotype, wherein the polymorphic nucleic acid is in a genomic region flanked by: loci NW0251455 (SEQ ID NO: 5) and NW0248583 (SEQ ID NO: 4) on linkage group 2 (LG2), or within 15 cM thereof; loci NW0249249 (SEQ ID NO: 9) and NW0249873 (SEQ ID NO: 11) on linkage group 4 (LG4), or within 15 cM thereof; loci NW0250227 (SEQ ID NO: 12) and NW0249974 (SEQ ID NO: 18) on linkage group 9 (LG9), or within 15 cM thereof; or loci NW0248282 (SEQ ID NO: 19) and NW0250036 (SEQ ID NO: 22) on linkage group 11 (LG11), or within 15 cM thereof. In another embodiment, the method further comprises the step of: (ii) identifying at least one watermelon plant in which a genotype associated with a desired seed size phenotype has been detected and denoting that the watermelon plant comprises a genotype associated with a desired seed size phenotype. The method may further comprise the step of: (iii) selecting a denoted watermelon plant from a population of plants. In the method, the desired seed size phenotype may comprise one or more seed traits selected from the group consisting of an average 100 seed weight; an average seed length; and an average seed width. In one embodiment, the desired seed size phenotype comprises an average 100 seed weight; an average seed length; and an average seed width.

In another embodiment of the invention, a method is provided involving detecting a genotype associated with a desired seed size phenotype based on the detection of a polymorphic nucleic acid located in a genomic region flanked by: loci NW0251455 (SEQ ID NO: 5) and NW0248118 (SEQ ID NO: 1) on LG2; loci NW0248118 (SEQ ID NO: 1) and NW0251236 (SEQ ID NO: 2) on LG2; loci NW0248118 (SEQ ID NO: 1) and NW0250242 (SEQ ID NO: 3) on LG2; loci NW0248118 (SEQ ID NO: 1) and NW0248583 (SEQ ID NO: 4) on LG2; loci NW0251236 (SEQ ID NO: 2) and NW0250242 (SEQ ID NO: 3) on LG2; loci NW0251236 (SEQ ID NO: 2) and NW0248583 (SEQ ID NO: 4) on LG2; loci NW0250242 (SEQ ID NO: 3) and NW0248583 (SEQ ID NO: 4) on LG2; loci NW0249249 (SEQ ID NO: 9) and NW0250697 (SEQ ID NO: 10) on LG4; loci NW0249249 (SEQ ID NO: 9) and NW0249873 (SEQ ID NO: 11) on LG4; loci NW0250697 (SEQ ID NO: 10) and NW0249873 (SEQ ID NO: 11) on LG4; loci NW0250227 (SEQ ID NO: 12) and NW0250857 (SEQ ID NO: 13) on LG9; loci NW0250227 (SEQ ID NO: 12) and NW0249185 (SEQ ID NO: 14) on LG9; loci NW0250227 (SEQ ID NO: 12) and NW0249226 (SEQ ID NO: 15) on LG9; loci NW0250227 (SEQ ID NO: 12) and NW0248254 (SEQ ID NO: 16) on LG9; loci NW0250227 (SEQ ID NO: 12) and NW0249883 (SEQ ID NO: 17) on LG9; loci NW0250227 (SEQ ID NO: 12) and NW0249974 (SEQ ID NO: 18) on LG9; loci NW0250857 (SEQ ID NO: 13) and NW0249185 (SEQ ID NO: 14) on LG9; loci NW0250857 (SEQ ID NO: 13) and NW0249226 (SEQ ID NO: 15) on LG9; loci NW0250857 (SEQ ID NO: 13) and NW0248254 (SEQ ID NO: 16) on LG9; loci NW0250857 (SEQ ID NO: 13) and NW0249883 (SEQ ID NO: 17) on LG9; loci NW0250857 (SEQ ID NO: 13) and NW0249974 (SEQ ID NO: 18) on LG9; loci NW0249185 (SEQ ID NO: 14) and NW0249226 (SEQ ID NO: 15) on LG9; loci NW0249185 (SEQ ID NO: 14) and NW0248254 (SEQ ID NO: 16) on LG9; loci NW0249185 (SEQ ID NO: 14) and NW0249883 (SEQ ID NO: 17) on LG9; loci NW0249185 (SEQ ID NO: 14) and NW0249974 (SEQ ID NO: 18) on LG9; loci NW0249226 (SEQ ID NO: 15) and NW0248254 (SEQ ID NO: 16) on LG9; loci NW0249226 (SEQ ID NO: 15) and NW0248254 (SEQ ID NO: 16) on LG9; loci NW0248254 (SEQ ID NO: 16) and NW0249883 (SEQ ID NO: 17) on LG9; loci NW0248254 (SEQ ID NO: 16) and NW0249974 (SEQ ID NO: 18) on LG9; loci NW0249883 (SEQ ID NO: 17) and NW0249974 (SEQ ID NO: 18) on LG9; loci NW0248282 (SEQ ID NO: 19) and NW0249891 (SEQ ID NO: 20) on LG11; loci NW0248282 (SEQ ID NO: 19) and NW0251129 (SEQ ID NO: 21) on LG11; loci NW0248282 (SEQ ID NO: 19) and NW0250036 (SEQ ID NO: 22) on LG11; loci NW0249891 (SEQ ID NO: 20) and NW0251129 (SEQ ID NO: 21) on LG11; loci NW0249891 (SEQ ID NO: 20) and NW0250036 (SEQ ID NO: 22) on LG11; or loci NW0251129 (SEQ ID NO: 21) and NW0250036 (SEQ ID NO: 22) on LG11; or within 15 cM thereof. In specific embodiments, at least one of said polymorphic nucleic acids is (i) selected from the group on LG2 consisting of NW0248118 (SEQ ID NO: 1); NW0251236 (SEQ ID NO: 2); NW0250242 (SEQ ID NO: 3); and NW0248583 (SEQ ID NO: 4); NW0251455 (SEQ ID NO: 5); NW0249783 (SEQ ID NO: 6); NW0250500 (SEQ ID NO: 7); NW0250854 (SEQ ID NO: 8); NW0249314 (SEQ ID NO: 23); (ii) selected from the group on LG4 consisting of NW0249249 (SEQ ID NO: 9); NW0250697 (SEQ ID NO: 10); and NW0249873 (SEQ ID NO: 11); (iii) selected from the group on LG9 consisting of NW0250227 (SEQ ID NO: 12); NW0250857 (SEQ ID NO: 13); NW0249185 (SEQ ID NO: 14); NW0249226 (SEQ ID NO: 15); NW0248254 (SEQ ID NO: 16); NW0249883 (SEQ ID NO: 17); and NW0249974 (SEQ ID NO: 18); or (iv) selected from the group on LG11 consisting of NW0248282 (SEQ ID NO: 19); NW0249891 (SEQ ID NO: 20); NW0251129 (SEQ ID NO: 21); or NW0250036 (SEQ ID NO: 22).

In yet another aspect, the invention provides a method for producing a watermelon plant that comprises in its genome at least one introgressed locus associated with a desired seed size phenotype, the method comprising: (i) crossing a first watermelon plant lacking a locus associated with a desired seed size phenotype with a second watermelon plant comprising: (a) an allele of at least one polymorphic nucleic acid that is associated with desired seed size phenotype located in a genomic region flanked by loci NW0251455 (SEQ ID NO: 5) and NW0248583 (SEQ ID NO: 4) on linkage group 2 (LG2), or within 15 cM thereof; loci NW0249249 (SEQ ID NO: 9) and NW0249873 (SEQ ID NO: 11) on linkage group 4 (LG4), or within 15 cM thereof; loci NW0250227 (SEQ ID NO: 12) and NW0249974 (SEQ ID NO: 18) on linkage group 9 (LG9), or within 15 cM thereof; or loci NW0248282 (SEQ ID NO: 19) and NW0250036 (SEQ ID NO: 22) on linkage group 11 (LG11), or within 15 cM thereof. (b) at least one additional polymorphic locus located outside of said region that is not present in said first watermelon plant, to obtain a population of watermelon plants segregating for the polymorphic locus that is associated with a desired seed size phenotype and said additional polymorphic locus; (ii) detecting said polymorphic locus in at least one watermelon plant from said population of watermelon plants, and (iii) selecting a watermelon plant comprising said locus associated with a desired seed size phenotype that lacks said additional polymorphic locus, thereby obtaining a watermelon plant comprising in its genome at least one introgressed allele of a polymorphic nucleic acid associated with a desired seed size phenotype. In the method, the selected watermelon plant may comprise an introgressed locus associated with a desired seed size or shape phenotype. The desired seed size phenotype may comprise one or more seed traits selected from the group consisting of an average 100 seed weight; an average seed length; and an average seed width. In one embodiment, the desired seed size phenotype comprises an average 100 seed weight; an average seed length; and an average seed width.

In particular embodiments of the invention, any introgressed locus associated with a desired seed size phenotype includes any one or more of a genomic region flanked by: loci NW0251455 (SEQ ID NO: 5) and NW0249783 (SEQ ID NO: 6) on LG2; loci NW0249783 (SEQ ID NO: 6) and NW0250500 (SEQ ID NO: 7) on LG2; loci NW0250500 (SEQ ID NO: 7) and NW0250854 (SEQ ID NO: 8) on LG2; loci NW0250854 (SEQ ID NO: 8) and NW0248118 (SEQ ID NO: 1) on LG2; loci NW0248118 (SEQ ID NO: 1) and NW0251236 (SEQ ID NO: 2) on LG2; loci NW0248118 (SEQ ID NO: 1) and NW0250242 (SEQ ID NO: 3) on LG2; loci NW0248118 (SEQ ID NO: 1) and NW0248583 (SEQ ID NO: 4) on LG2; loci NW0251236 (SEQ ID NO: 2) and NW0250242 (SEQ ID NO: 3) on LG2; loci NW0251236 (SEQ ID NO: 2) and NW0248583 (SEQ ID NO: 4) on LG2; loci NW0250242 (SEQ ID NO: 3) and NW0248583 (SEQ ID NO: 4) on LG2; loci NW0249249 (SEQ ID NO: 9) and NW0250697 (SEQ ID NO: 10) on LG4; loci NW0249249 (SEQ ID NO: 9) and NW0249873 (SEQ ID NO: 11) on LG4; loci NW0250697 (SEQ ID NO: 10) and NW0249873 (SEQ ID NO: 11) on LG4; loci NW0250227 (SEQ ID NO: 12) and NW0250857 (SEQ ID NO: 13) on LG9; loci NW0250227 (SEQ ID NO: 12) and NW0249185 (SEQ ID NO: 14) on LG9; loci NW0250227 (SEQ ID NO: 12) and NW0249226 (SEQ ID NO: 15) on LG9; loci NW0250227 (SEQ ID NO: 12) and NW0248254 (SEQ ID NO: 16) on LG9; loci NW0250227 (SEQ ID NO: 12) and NW0249883 (SEQ ID NO: 17) on LG9; loci NW0250227 (SEQ ID NO: 12) and NW0249974 (SEQ ID NO: 18) on LG9; loci NW0250857 (SEQ ID NO: 13) and NW0249185 (SEQ ID NO: 14) on LG9; loci NW0250857 (SEQ ID NO: 13) and NW0249226 (SEQ ID NO: 15) on LG9; loci NW0250857 (SEQ ID NO: 13) and NW0248254 (SEQ ID NO: 16) on LG9; loci NW0250857 (SEQ ID NO: 13) and NW0249883 (SEQ ID NO: 17) on LG9; loci NW0250857 (SEQ ID NO: 13) and NW0249974 (SEQ ID NO: 18) on LG9; loci NW0249185 (SEQ ID NO: 14) and NW0249226 (SEQ ID NO: 15) on LG9; loci NW0249185 (SEQ ID NO: 14) and NW0248254 (SEQ ID NO: 16) on LG9; loci NW0249185 (SEQ ID NO: 14) and NW0249883 (SEQ ID NO: 17) on LG9; loci NW0249185 (SEQ ID NO: 14) and NW0249974 (SEQ ID NO: 18) on LG9; loci NW0249226 (SEQ ID NO: 15) and NW0248254 (SEQ ID NO: 16) on LG9; loci NW0248254 (SEQ ID NO: 16) and NW0249883 (SEQ ID NO: 17) on LG9; loci NW0248254 (SEQ ID NO: 16) and NW0249974 (SEQ ID NO: 18) on LG9; loci NW0249883 (SEQ ID NO: 17) and NW0249974 (SEQ ID NO: 18) on LG9; loci NW0248282 (SEQ ID NO: 19) and NW0249891 (SEQ ID NO: 20) on LG11; loci NW0248282 (SEQ ID NO: 19) and NW0251129 (SEQ ID NO: 21) on LG11; loci NW0248282 (SEQ ID NO: 19) and NW0250036 (SEQ ID NO: 22) on LG11; loci NW0249891 (SEQ ID NO: 20) and NW0251129 (SEQ ID NO: 21) on LG11; loci NW0249891 (SEQ ID NO: 20) and NW0250036 (SEQ ID NO: 22) on LG11; or loci NW0251129 (SEQ ID NO: 21) and NW0250036 (SEQ ID NO: 22) on LG11; or within 15 cM thereof.

In still yet another aspect, the invention provides a watermelon plant produced by any method of the invention, including any progeny plants of any generation therefrom that comprises an introgressed locus associated with a desired seed size phenotype. Parts of such a plant are also provided. Plant parts include as pollen, an ovule, a leaf, an embryo, a root, a root tip, an anther, a flower, a fruit, a stem, a shoot, a seed, a protoplast, a cell, and a callus. The seed of such a plant are also provided.

In still yet another aspect, the invention provides a method of watermelon plant breeding, the method comprising the steps of: (i) selecting at least a first watermelon plant comprising at least one allele of a polymorphic nucleic acid that is genetically linked to a QTL associated with a desired seed size phenotype, wherein the QTL maps to a position between loci NW0251455 (SEQ ID NO: 5) and NW0248583 (SEQ ID NO: 4) on linkage group 2 (LG2); loci NW0249249 (SEQ ID NO: 9) and NW0249873 (SEQ ID NO: 11) on linkage group 4 (LG4); loci NW0250227 (SEQ ID NO: 12) and NW0249974 (SEQ ID NO: 18) on linkage group 9 (LG9); or loci NW0248282 (SEQ ID NO: 19) and NW0250036 (SEQ ID NO: 22) on linkage group 11 (LG11); and (ii) crossing the first watermelon plant with itself or a second watermelon plant to produce progeny watermelon plants comprising the QTL associated with a desired seed size phenotype. In one embodiment, the desired seed size phenotype comprises one or more seed traits selected from the group consisting of an average 100 seed weight; an average seed length; and an average seed width. In other embodiments, the desired seed size phenotype comprises an average 100 seed weight; an average seed length; and an average seed width. In particular embodiments, the QTL maps to a position between: loci NW0251455 (SEQ ID NO: 5) and NW0249783 (SEQ ID NO: 6) on LG2; loci NW0249783 (SEQ ID NO: 6) and NW0250500 (SEQ ID NO: 7) on LG2; loci NW0250500 (SEQ ID NO: 7) and NW0250854 (SEQ ID NO: 8) on LG2; loci NW0250854 (SEQ ID NO: 8) and NW0248118 (SEQ ID NO: 1) on LG2; loci NW0248118 (SEQ ID NO: 1) and NW0251236 (SEQ ID NO: 2) on LG2; loci NW0248118 (SEQ ID NO: 1) and NW0250242 (SEQ ID NO: 3) on LG2; loci NW0248118 (SEQ ID NO: 1) and NW0248583 (SEQ ID NO: 4) on LG2; loci NW0251236 (SEQ ID NO: 2) and NW0250242 (SEQ ID NO: 3) on LG2; loci NW0251236 (SEQ ID NO: 2) and NW0248583 (SEQ ID NO: 4) on LG2; loci NW0250242 (SEQ ID NO: 3) and NW0248583 (SEQ ID NO: 4) on LG2; loci NW0249249 (SEQ ID NO: 9) and NW0250697 (SEQ ID NO: 10) on LG4; loci NW0249249 (SEQ ID NO: 9) and NW0249873 (SEQ ID NO: 11) on LG4; loci NW0250697 (SEQ ID NO: 10) and NW0249873 (SEQ ID NO: 11) on LG4; loci NW0250227 (SEQ ID NO: 12) and NW0250857 (SEQ ID NO: 13) on LG9; loci NW0250227 (SEQ ID NO: 12) and NW0249185 (SEQ ID NO: 14) on LG9; loci NW0250227 (SEQ ID NO: 12) and NW0249226 (SEQ ID NO: 15) on LG9; loci NW0250227 (SEQ ID NO: 12) and NW0248254 (SEQ ID NO: 16) on LG9; loci NW0250227 (SEQ ID NO: 12) and NW0249883 (SEQ ID NO: 17) on LG9; loci NW0250227 (SEQ ID NO: 12) and NW0249974 (SEQ ID NO: 18) on LG9; loci NW0250857 (SEQ ID NO: 13) and NW0249185 (SEQ ID NO: 14) on LG9; loci NW0250857 (SEQ ID NO: 13) and NW0249226 (SEQ ID NO: 15) on LG9; loci NW0250857 (SEQ ID NO: 13) and NW0248254 (SEQ ID NO: 16) on LG9; loci NW0250857 (SEQ ID NO: 13) and NW0249883

(SEQ ID NO: 17) on LG9; loci NW0250857 (SEQ ID NO: 13) and NW0249974 (SEQ ID NO: 18) on LG9; loci NW0249185 (SEQ ID NO: 14) and NW0249226 (SEQ ID NO: 15) on LG9; loci NW0249185 (SEQ ID NO: 14) and NW0248254 (SEQ ID NO: 16) on LG9; loci NW0249185 (SEQ ID NO: 14) and NW0249883 (SEQ ID NO: 17) on LG9; loci NW0249185 (SEQ ID NO: 14) and NW0249974 (SEQ ID NO: 18) on LG9; loci NW0249226 (SEQ ID NO: 15) and NW0248254 (SEQ ID NO: 16) on LG9; loci NW0248254 (SEQ ID NO: 16) and NW0249883 (SEQ ID NO: 17) on LG9; loci NW0248254 (SEQ ID NO: 16) and NW0249974 (SEQ ID NO: 18) on LG9; loci NW0249883 (SEQ ID NO: 17) and NW0249974 (SEQ ID NO: 18) on LG9; loci NW0248282 (SEQ ID NO: 19) and NW0249891 (SEQ ID NO: 20) on LG11; loci NW0248282 (SEQ ID NO: 19) and NW0251129 (SEQ ID NO: 21) on LG11; loci NW0248282 (SEQ ID NO: 19) and NW0250036 (SEQ ID NO: 22) on LG11; loci NW0249891 (SEQ ID NO: 20) and NW0251129 (SEQ ID NO: 21) on LG11; loci NW0249891 (SEQ ID NO: 20) and NW0250036 (SEQ ID NO: 22) on LG11; or loci NW0251129 (SEQ ID NO: 21) and NW0250036 (SEQ ID NO: 22) on LG11.

In one embodiment of a method of the invention, a polymorphic nucleic acid is genetically linked to a QTL associated with a desired seed size phenotype that is: (i) selected from the group on LG2 consisting of NW0248118 (SEQ ID NO: 1); NW0251236 (SEQ ID NO: 2); NW0250242 (SEQ ID NO: 3); and NW0248583 (SEQ ID NO: 4); NW0251455 (SEQ ID NO: 5); NW0249783 (SEQ ID NO: 6); NW0250500 (SEQ ID NO: 7); NW0250854 (SEQ ID NO: 8); NW0249314 (SEQ ID NO: 23); (ii) selected from the group on LG4 consisting of NW0249249 (SEQ ID NO: 9); NW0250697 (SEQ ID NO: 10); and NW0249873 (SEQ ID NO: 11); (iii) selected from the group on LG9 consisting of NW0250227 (SEQ ID NO: 12); NW0250857 (SEQ ID NO: 13); NW0249185 (SEQ ID NO: 14); NW0249226 (SEQ ID NO: 15); NW0248254 (SEQ ID NO: 16); NW0249883 (SEQ ID NO: 17); and NW0249974 (SEQ ID NO: 18); or (iv) selected from the group on LG11 consisting of NW0248282 (SEQ ID NO: 19); NW0249891 (SEQ ID NO: 20); NW0251129 (SEQ ID NO: 21); or NW0250036 (SEQ ID NO: 22). In one embodiment, at least one polymorphic nucleic acid that is genetically linked to a QTL associated with a desired seed size phenotype maps within 40 cM, 20 cM, 15 cM, 10 cM, 5 cM, or 1 cM of the QTL associated with a desired seed size phenotype.

In still yet another aspect, a method is provided for introgressing an allele into a watermelon plant, the method comprising: (i) providing a population of watermelon plants; (ii) genotyping at least one watermelon plant in the population with respect to at least one polymorphic nucleic acid located in a genomic region flanked by loci NW0251455 (SEQ ID NO: 5) and NW0248583 (SEQ ID NO: 4) on linkage group 2 (LG2); loci NW0249249 (SEQ ID NO: 9) and NW0249873 (SEQ ID NO: 11) on linkage group 4 (LG4); loci NW0250227 (SEQ ID NO: 12) and NW0249974 (SEQ ID NO: 18) on linkage group 9 (LG9); or loci NW0248282 (SEQ ID NO: 19) and NW0250036 (SEQ ID NO: 22) on linkage group 11 (LG11); and (iii) selecting from the population at least one watermelon plant comprising at least one allele associated with a desired seed size phenotype. In certain embodiments, the desired seed size phenotype comprises one or more seed traits selected from the group consisting of an average 100 seed weight; an average seed length; and an average seed width. In other embodiments, the desired seed size phenotype comprises an average 100 seed weight; an average seed length; and an average seed width. The polymorphic nucleic acid may in certain embodiments be located in a genomic region flanked by: loci NW0251455 (SEQ ID NO: 5) and NW0249783 (SEQ ID NO: 6) on LG2; loci NW0249783 (SEQ ID NO: 6) and NW0250500 (SEQ ID NO: 7) on LG2; loci NW0250500 (SEQ ID NO: 7) and NW0250854 (SEQ ID NO: 8) on LG2; loci NW0250854 (SEQ ID NO: 8) and NW0248118 (SEQ ID NO: 1) on LG2; loci NW0248118 (SEQ ID NO: 1) and NW0251236 (SEQ ID NO: 2) on LG2; loci NW0248118 (SEQ ID NO: 1) and NW0250242 (SEQ ID NO: 3) on LG2; loci NW0248118 (SEQ ID NO: 1) and NW0248583 (SEQ ID NO: 4) on LG2; loci NW0251236 (SEQ ID NO: 2) and NW0250242 (SEQ ID NO: 3) on LG2; loci NW0251236 (SEQ ID NO: 2) and NW0248583 (SEQ ID NO: 4) on LG2; loci NW0250242 (SEQ ID NO: 3) and NW0248583 (SEQ ID NO: 4) on LG2; loci NW0249249 (SEQ ID NO: 9) and NW0250697 (SEQ ID NO: 10) on LG4; loci NW0249249 (SEQ ID NO: 9) and NW0249873 (SEQ ID NO: 11) on LG4; loci NW0250697 (SEQ ID NO: 10) and NW0249873 (SEQ ID NO: 11) on LG4; loci NW0250227 (SEQ ID NO: 12) and NW0250857 (SEQ ID NO: 13) on LG9; loci NW0250227 (SEQ ID NO: 12) and NW0249185 (SEQ ID NO: 14) on LG9; loci NW0250227 (SEQ ID NO: 12) and NW0249226 (SEQ ID NO: 15) on LG9; loci NW0250227 (SEQ ID NO: 12) and NW0248254 (SEQ ID NO: 16) on LG9; loci NW0250227 (SEQ ID NO: 12) and NW0249883 (SEQ ID NO: 17) on LG9; loci NW0250227 (SEQ ID NO: 12) and NW0249974 (SEQ ID NO: 18) on LG9; loci NW0250857 (SEQ ID NO: 13) and NW0249185 (SEQ ID NO: 14) on LG9; loci NW0250857 (SEQ ID NO: 13) and NW0249226 (SEQ ID NO: 15) on LG9; loci NW0250857 (SEQ ID NO: 13) and NW0248254 (SEQ ID NO: 16) on LG9; loci NW0250857 (SEQ ID NO: 13) and NW0249883 (SEQ ID NO: 17) on LG9; loci NW0250857 (SEQ ID NO: 13) and NW0249974 (SEQ ID NO: 18) on LG9; loci NW0249185 (SEQ ID NO: 14) and NW0249226 (SEQ ID NO: 15) on LG9; loci NW0249185 (SEQ ID NO: 14) and NW0248254 (SEQ ID NO: 16) on LG9; loci NW0249185 (SEQ ID NO: 14) and NW0249883 (SEQ ID NO: 17) on LG9; loci NW0249185 (SEQ ID NO: 14) and NW0249974 (SEQ ID NO: 18) on LG9; loci NW0249226 (SEQ ID NO: 15) and NW0248254 (SEQ ID NO: 16) on LG9; loci NW0249226 (SEQ ID NO: 15) and NW0248254 (SEQ ID NO: 16) on LG9; loci NW0248254 (SEQ ID NO: 16) and NW0249883 (SEQ ID NO: 17) on LG9; loci NW0248254 (SEQ ID NO: 16) and NW0249974 (SEQ ID NO: 18) on LG9; loci NW0249883 (SEQ ID NO: 17) and NW0249974 (SEQ ID NO: 18) on LG9; loci NW0248282 (SEQ ID NO: 19) and NW0249891 (SEQ ID NO: 20) on LG11; loci NW0248282 (SEQ ID NO: 19) and NW0251129 (SEQ ID NO: 21) on LG11; loci NW0248282 (SEQ ID NO: 19) and NW0250036 (SEQ ID NO: 22) on LG11; loci NW0249891 (SEQ ID NO: 20) and NW0251129 (SEQ ID NO: 21) on LG11; loci NW0249891 (SEQ ID NO: 20) and NW0250036 (SEQ ID NO: 22) on LG11; or loci NW0251129 (SEQ ID NO: 21) and NW0250036 (SEQ ID NO: 22) on LG11. In one embodiment, at least one of said polymorphic nucleic acid is: (i) selected from the group on LG2 consisting of NW0248118 (SEQ ID NO: 1); NW0251236 (SEQ ID NO: 2); NW0250242 (SEQ ID NO: 3); and NW0248583 (SEQ ID NO: 4); NW0251455 (SEQ ID NO: 5); NW0249783 (SEQ ID NO: 6); NW0250500 (SEQ ID NO: 7); NW0250854 (SEQ ID NO: 8); NW0249314 (SEQ ID NO: 23); (ii) selected from the group on LG4 consisting of NW0249249 (SEQ ID NO: 9); NW0250697 (SEQ ID NO: 10); and NW0249873 (SEQ ID NO: 11); (iii) selected from the group on LG9 consisting of NW0250227 (SEQ ID NO:

12); NW0250857 (SEQ ID NO: 13); NW0249185 (SEQ ID NO: 14); NW0249226 (SEQ ID NO: 15); NW0248254 (SEQ ID NO: 16); NW0249883 (SEQ ID NO: 17); and NW0249974 (SEQ ID NO: 18); or (iv) selected from the group on LG11 consisting of NW0248282 (SEQ ID NO: 19); NW0249891 (SEQ ID NO: 20); NW0251129 (SEQ ID NO: 21); or NW0250036 (SEQ ID NO: 22).

Other objects and features will be in part apparent and in part pointed out hereinafter.

BRIEF DESCRIPTION OF THE DRAWINGS

(FIG. 1A) Klondike Black Seeded (KBS) and New Hampshire Midget (NHM), and (FIG. 1B) ZWRM50 (PI 593359; ZWRM) and PI 244019 (*Citroides*).

BRIEF DESCRIPTION OF THE SEQUENCES

Figure 1A:
FIGS. 1A, 1B shows a series of photographic images illustrating seed phenotypes of the parents of two mapping populations.

SEQ ID NO: 1—NW0248118 DNA sequence
SEQ ID NO: 2—NW0251236 DNA sequence
SEQ ID NO: 3—NW0250242 DNA sequence
SEQ ID NO: 4—NW0248583 DNA sequence
SEQ ID NO: 5—NW0251455 DNA sequence.
SEQ ID NO: 6—NW0249783 DNA sequence
SEQ ID NO: 7—NW0250500 DNA sequence
SEQ ID NO: 8—NW0250854 DNA sequence
SEQ ID NO: 9—NW0249249 DNA sequence
SEQ ID NO: 10—NW0250697 DNA sequence
SEQ ID NO: 11—NW0249873 DNA sequence
SEQ ID NO: 12—NW0250227 DNA sequence
SEQ ID NO: 13—NW0250857 DNA sequence
SEQ ID NO: 14—NW0249185 DNA sequence
SEQ ID NO: 15—NW0249226 DNA sequence
SEQ ID NO: 16—NW0248254 DNA sequence
SEQ ID NO: 17—NW0249883 DNA sequence
SEQ ID NO: 18—NW0249974 DNA sequence
SEQ ID NO: 19—NW0248282 DNA sequence
SEQ ID NO: 20—NW0249891 DNA sequence
SEQ ID NO: 21—NW0251129 DNA sequence
SEQ ID NO: 22—NW0250036 DNA sequence
SEQ ID NO: 23—NW0249314 DNA sequence

DETAILED DESCRIPTION OF THE INVENTION

Headings are provided herein solely for ease of reading and should not be interpreted as limiting.

I. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seeds, leaves, stems, and the like.

As used herein, a watermelon having a "desired seed size phenotype" has one or more traits of a desired average or range of 100 seed weight, average or range of seed length, or average or range of seed width.

As used herein, the phrase "100 seed weight" or "100SWT" refers to the weight of 100 seeds, represented here in the unit of grams (g).

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for alleles that affect the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "introgressed," when used in reference to a genetic locus, refers to a genetic locus that has been introduced into a new genetic background. Introgression of a genetic locus can thus be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, the term "maturity" means maturity of fruit development. Maturity indicates the time a watermelon fruit is ready to be harvested. In watermelon, the maturity comes associated with changes in flesh color and sugar content.

As used herein, the term "denoting" when used in reference to a plant genotype refers to any method whereby a plant is indicated to have a certain genotype. This includes any means of identification of a plant having a certain genotype. Indication of a certain genotype may include, but is not limited to, any entry into any type of written or electronic medium or database whereby the plant's genotype is provided. Indications of a certain genotype may also include, but are not limited to, any method where a plant is physically marked or tagged. Illustrative examples of physical marking or tags useful in the invention include, but are not limited to, a barcode, a radio-frequency identification (RFID), a label, or the like.

II. Overview

The invention represents an advance in the art in that it permits development of watermelon varieties with desired seed size phenotypes. Seed size is significant because watermelon breeders aim to develop hybrid cultivars with large seed for planting (especially where direct seeding is used), but that will produce fruit with small seed. In some parts of the world, such as Nigeria and China, *C. lanatus* is grown, not for its edible flesh, but its edible seeds (e.g., "egusi"), where increased seed size and width (e.g., ~11 mm) can be desirable. Thus, there are different market requirements for particular groups of breeders, growers and consumers. For example, a watermelon breeder may thus develop in accordance with the invention hybrid cultivars with large seed for planting (e.g., where direct seeding is used), but producing fruit with small seed. Such strategy can be followed to minimize the size of the white seed coat in the seedless fruit.

Certain embodiments of the present invention thus provide watermelon plants comprising in their genome at least a first introgressed locus contributing to a desired seed size phenotype. In accordance with the invention the introgressed locus allele may not previously have been introgressed into the given genomic background of the specific variety or cultivar developed. For example, as discussed further below, a watermelon having a desired seed size phenotype can have one or more traits selected from seed weight (such as measured by 100 seed weight), seed length, or seed width, and any and all combinations thereof. Certain embodiments provide for methods of detecting in a watermelon plant a genotype associated with the desired seed size phenotype. Certain embodiments also provide methods of identifying and selecting a watermelon plant comprising in its genome a genotype associated with a desired seed size phenotype. Further, certain embodiments provide methods of producing a watermelon plant that comprises in its genome at least one introgressed locus associated with a desired seed size phenotype and methods for introgressing such an allele into a watermelon plant. Watermelon plants and parts thereof made by any of said methods are also provided for in certain embodiments of the invention as well as polymorphic nucleic acid sequences that may be used in the production and identification of such plants By providing markers to infer a seed size phenotype of interest, the invention results in significant economization by substituting costly and time-intensive phenotyping assays with genotyping. Further, breeding programs can be designed to explicitly drive the frequency of specific favorable phenotypes by targeting particular genotypes. Fidelity of these associations may be monitored continuously to ensure maintained predictive ability and, thus, informed breeding decisions.

In accordance with the invention, one of skill in the art may thus identify a candidate germplasm source possessing a desirable seed size phenotype as described herein, but which is lacking one or more traits which the plant breeder seeks to have in a variety or parent line thereof. The techniques of the invention may be used to identify desirable seed size phenotypes by identifying genetic markers associated with the phenotype, or such techniques may employ phenotypic assays to identify desired plants either alone or in combination with genetic assays, thereby also identifying a marker genotype associated with the trait that may be used for production of new varieties with the methods described herein.

Generally, watermelon seed size can be divided into qualitative categories as being large (e.g., 13 mm), medium (e.g., 10 mm), small (e.g., 6 mm), tomato (e.g., approximately the same size as tomato seed), or tiny (smaller than 5 mm, but larger than tomato seed size) (see, e.g., Poole, C. F., P. C. Grimball, and D. R. Porter. 1941. Inheritance of seed characters in watermelon. J. Agr. Res 63:433-456; Gusmini, G. 2005. Inheritance of fruit characteristics and disease resistance in watermelon [*Citrullus lanatus* (Thunb.) Matsum. & Nakai]. North Carolina State University, Raleigh, N.C., Doctor of Philosophy; Wehner, T. C., N. V. Shetty, and G. W. Elmstron. 2001. Breeding and seed production, p. 27-73. In: Maynard, D. N. (ed.), Watermelons: Characteristics, production, and marketing. ASHS Press, Alexandria, Va.). Without being bound by any particular theory, seed size in watermelon is thought to be controlled by two genes with epistatic interaction.

In accordance with the invention, a desired seed size phenotype refers to any seed weight, seed length or seed width phenotype that one or more breeder, grower or consumer may find advantageous for certain applications. As explained, in certain aspects, a large seed size phenotype may be desirable for applications including, but not necessarily limited to direct seed planting and as a food or feed source. Small seed size may be desirable for fruit quality applications, for example, and it may be desirable to produce hybrids that can be grown from relatively larger seeds, but produce fruit with smaller seeds. It may also be desired to produce seed with greater or lesser length and width, including seeds that are more rounded or squared in shape, relative to those that are relatively longer and thinner, or those that overall are longer and wider, either with a relatively thinner or thicker seed, this producing a relatively lighter or heavier seed as in relation to length and width. Again, the particular phenotype may depend upon the desired end uses. However, as the traits in question have been shown to be controlled by the QTL regions identified herein, these traits may be introgressed into desired genetic backgrounds using the methods of the invention.

Specific examples of seed size phenotypes provided merely for illustrative purposes include, for example, an average 100 seed weight of about 4.3 grams (see e.g., Example 4). As another non-limiting example, a watermelon variety can have an average seed length of about 7.5 millimeters (see e.g., Example 4). As yet another example, a watermelon variety can have an average seed width of about 4.1 millimeters (see e.g., Example 4).

Consistent with the foregoing, it has been known that seed weight, seed length and seed width are highly correlated (e.g., r=~0.9), even though the molecular tools and QTL provided herein have not been identified (see e.g., Hawkins, L. K., F. Dane, and T. L. Kubisiak. 2001. Molecular markers associated with morphological traits in watermelon. HortScience 36:1318-1322; Poole, C. F., P. C. Grimball, and D. R. Porter. 1941. Inheritance of seed characters in watermelon. J. Agr. Res 63:433-456; Zhang, X. P., B. B. Rhodes, and M. Wang. 1995. Genes controlling watermelon seed size, p. 144-147. In: Lester, G. and Dunlap, J. (eds.), Cucurbitaceae '94: Evaluation and Enhancement of Cucurbit Germplasm. ASHS Press, Alexandria, Va.). As shown herein, correlations between seed weight, seed length and seed width were statistically significant and high in both tested populations, but somewhat higher in the ZWRM×Citroides population than in the KBS×NHM population (Table 1). Thus, a watermelon having a desired seed size phenotype can have one or more traits of a desired average or range of 100 seed weight, average or range of seed length, or average or range of seed width.

The invention thus provides for the introgression of at least a first locus conferring a desired seed size phenotype into a given genetic background. Successful watermelon production depends on attention to various horticultural practices. These include soil management with special attention to proper fertilization, crop establishment with appropriate spacing, weed control, the introduction of bees or other insects for pollination, irrigation, pest management, and, if producing fruit from triploid plants, a suitable pollen source for producing seedless (triploid) watermelon. Watermelon fruit size and shape; rind color, thickness and toughness; seed size, color, and number; flesh color, texture, and sugar content; and freedom from fruit defects are all important characteristics to be considered in selection of watermelon varieties.

Watermelon crops can be established from seed or from transplants. Transplanting can result in an earlier crop compared with a crop produced from direct seeding. When a grower wants to raise a seedless fruited crop, transplanting can be preferred. Transplanting helps achieve complete plant stands rapidly, especially where higher seed costs, as with triploid seeds, make direct-seeding risky.

Watermelon breeders are challenged with anticipating changes in growing conditions, new pathogen pressure, and changing consumer preferences. With these projections, a breeder will attempt to create new cultivars that will fit the developing needs of growers, shippers, retailers, and consumers. Thus, the breeder is challenged to combine in a single genotype as many favorable attributes as possible for good growing distribution and eating.

III. Development of Watermelon Varieties with Desired Seed Size Phenotypes

As indicated, seed size is important in terms of fruit quality, and has significance to growers, processors, retailers, and customers. The current inventors have identified a quantitative trait locus (QTL) with major effects for seed size, as well as single nucleotide polymorphism (SNP) markers in the proximity of this locus that can be used for the tracking and introgression of this genomic region to desirable germplasm, such as by marker-assisted selection and/or marker-assisted backcrossing. As reported herein, a recombinant inbred line population (RIL, $F_6$) was developed by single seed descent from a cross between the elite cultivars (*C. lanatus* var. *lanatus*) Klondike Black Seeded (KBS; PI 635609) and New Hampshire Midget (NHM; PI 635617) and an $F_2$ population was created from a cross between an elite cultivar from China (ZWRM50; PI 593359) and a wild *C. lanatus* var. *citroides* accession from South Africa (*Citroides*; PI 244019). The Klondike Black Seeded× New Hampshire Midget (KBS×NHM) recombinant inbred line (RIL) population and the ZWRM50×PI 244019 (ZWRM×*Citroides*) $F_2$ population were used to identify main effect quantitative trait loci (M-QTL) and epistatic QTL (E-QTL) associated with 100 seed weight (100SWT), seed length (SL) and seed width (SWD).

Figure 3:
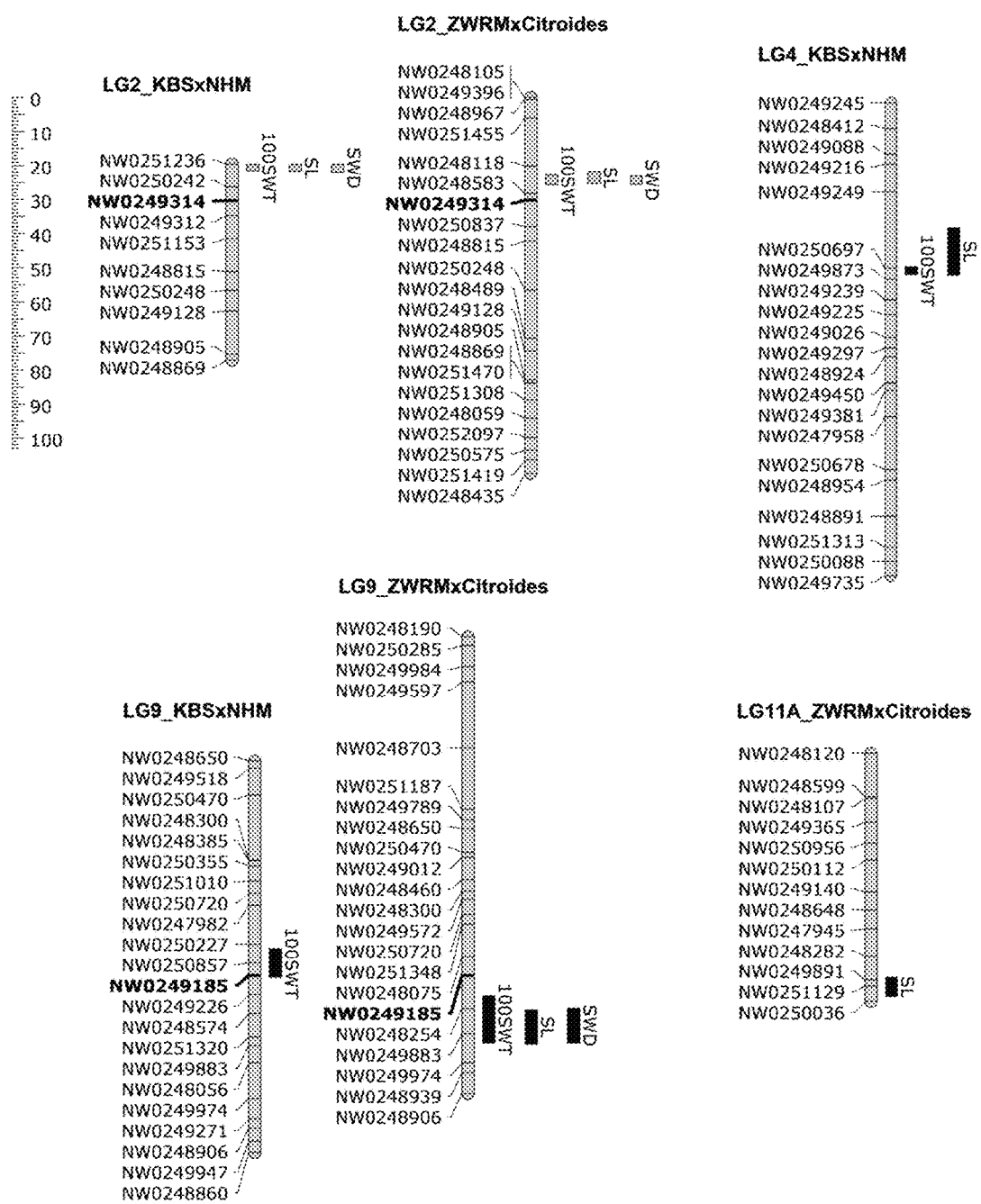
FIG. 3 is a chart showing QTL identified for the three traits in the Klondike Black Seeded×New Hampshire Midget population (KBS×NHM), and the ZWRM50×PI 244019 (ZWRM×*Citroides*) populations, where QTLs are indicated as bars. The length of the bar is equal to the 1-LOD support interval. Solid and shaded bars represent loci where the maternal parent and paternal parent contribute the additive effect, respectively. A common marker close to the QTL is shown in bold to facilitate positional comparisons between populations. The cM scale and the figure were produced using MapChart version 2.1 (Voorrips, R. E. 2002. MapChart: Software for the graphical presentation of linkage maps and QTLs. The Journal of Heredity 93:77-78).

From genetic maps of *C. lanatus* having 378 markers for the KBS×NHM population and 338 markers for the ZWRM×*Citroides* population, QTL mapping analysis in the two populations identified a total of 13 QTL on four LGs for the three traits of seed weight, seed length and seed width (Table 2, FIG. 3). The consistently high correlation between these traits suggest pleotropism.

Major M-QTL ($R^2$=26.9-73.6%) were identified at the same location on LG 2 in both populations for all three traits. Minor and intermediate M-QTL for all three traits co-localized on LG 9 in the ZWRM×*Citroides* population and on LG 4 for 100SWT and SL in the KBS×NHM population. While significant epistatic effects were found between the M-QTL on LG2 and LG4 in the KBS×NHM population and between LG 2 and LG 9 in the ZWRM×*Citroides* population, the phenotypic variance explained by the E-QTL was generally small.

The invention thus contemplates the tracking and introduction of any such QTL and any combinations thereof into a given genetic background. One of ordinary skill will understand that any desired seed size phenotype including one or more traits of seed weight, seed length, and seed width can be introgressed from one genotype to another using a primary locus described herein via marker assisted selection. Accordingly, a germplasm source can be selected that has a desired seed size phenotype in terms of seed weight, seed length, or seed width. A breeder can now select a desired seed size phenotype or track such desired seed size phenotype during breeding using marker assisted selection for the region described herein. Provided with the present disclosure, one of ordinary skill can introduce a desired seed size phenotype into any genetic background.

Thus, QTL identified herein, such as the stable M-QTL on LG 2, can be used for marker assisted selection for seed size in watermelon. This discovery of seed size QTL will facilitate the development of watermelon having desired seed size phenotypes.

For most breeding objectives, commercial breeders work within germplasm that is often referred to as the "cultivated type." This germplasm is easier to breed with because it generally performs well when evaluated for horticultural performance. The performance advantage the cultivated type provides is sometimes offset by a lack of allelic diversity. This is the tradeoff a breeder accepts when working with cultivated germplasm—better overall performance, but a lack of allelic diversity. Breeders generally accept this tradeoff because progress is faster when working with cultivated material than when breeding with genetically diverse sources.

In contrast, when a breeder makes either intra-specific crosses, or interspecific crosses, a converse trade off occurs. In these examples, a breeder typically crosses cultivated germplasm with a non-cultivated type. In such crosses, the breeder can gain access to novel alleles from the non-cultivated type, but may have to overcome the genetic drag associated with the donor parent. Because of the difficulty with this breeding strategy, this approach often fails because of fertility and fecundity problems. The difficulty with this breeding approach extends to many crops, and is exemplified with an important disease resistant phenotype that was first described in tomato in 1944 (Smith, Proc. Am. Soc. Hort. Sci. 44:413-16). In this cross, a nematode disease resistance was transferred from *L. peruvianum* (PI128657) into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent. This allows the remaining genetic drag to be masked. The inventiveness of succeeding in this breeding approach has been recognized by the USPTO (U.S. Pat. Nos. 6,414,226, 6,096,944, 5,866,764, and 6,639,132).

In watermelon, the plant introduction accessions are typically lines that produce fruits with undesirable production and eating qualities. Even though these lines have poor horticultural qualities, some watermelon breeders, like some other crop breeders, attempt to breed with these PI lines because they potentially contain novel alleles. To date, the most commonly attempted breeding objective for use of the PI lines is to introgress new disease resistance genes. The process of introgressing novel resistance genes from the PI lines into acceptable commercial types is a long and often arduous process. This process can be difficult because the trait may be polygenic, or have low heritability, or have linkage drag or some combination thereof.

Some phenotypes are determined by the genotype at one locus. These simple traits, like those studied by Gregor Mendel, fall in discontinuous categories such as green or yellow seeds. Most variation observed in nature, however, is continuous, like yield in field corn, or human blood pressure. Unlike simply inherited traits, continuous variation can be the result of polygenic inheritance. Loci that affect continuous variation are referred to as quantitative trait loci (QTLs). Variation in the phenotype of a quantitative trait is the result of the allelic composition at the QTLs and the environmental effect. The heritability of a trait is the proportion of the phenotypic variation attributed to the genetic variance. This ratio varies between 0 and 1.0. Thus, a trait with heritability near 1.0 is not greatly affected by the environment. Those skilled in the art recognize the importance of creating commercial lines with high heritability horticultural traits because these cultivars will allow growers to produce a crop with uniform market specifications.

IV. Genomic Region, QTL, Polymorphic Nucleic Acids, and Alleles Associated with Watermelon Seed Size Phenotype Applicants have discovered a genomic region, QTL, alleles, polymorphic nucleic acids, linked markers, and the like that when present in certain allelic forms are associated with watermelon seed size phenotype.

Using two populations (KBS×NHM and ZWRM×*Citroides*), thirteen M-QTL were identified on four LGs (LG2, LG4, LG9, LG11) for the three traits of seed weight, seed length, and seed width.

LG2

One genomic region associated with a desired seed size phenotype is located at watermelon linkage group 2 and, on the genetic map of the KBS×NHM population, flanked by loci NW0251236 (SEQ ID NO: 2) and NW0250242 (SEQ ID NO: 3); and on the genetic map of the ZWRM×*Citroides* population, flanked by loci NW0248118 (SEQ ID NO: 1) and NW0248583 (SEQ ID NO: 4). Loci NW0249314 (SEQ ID NO: 23) was identified on LG2 in both the KBS×NHM population and the ZWRM×*Citroides* population (see e.g, FIG. 3). It is noted that marker order and distances between markers for the consensus map was calculated based on common markers between maps, rather than recombination frequencies (see e.g., Example 3, Example 4, FIG. 3).

A major watermelon seed size QTL was found to be located within this region. Certain of the various embodiments of the present disclosure utilize a QTL or polymorphic nucleic acid marker or allele located in this genomic region. Flanking markers on LG2 that identify a genomic region associated with a desired seed size phenotype include loci NW0248118 (SEQ ID NO: 1) and NW0248583 (SEQ ID NO: 4). Intervening markers on LG2 that identify a genomic region associated with a desired seed size phenotype include NW0251236 (SEQ ID NO: 2) and NW0250242 (SEQ ID NO: 3). This genomic region, or subregions thereof, associated with a desired seed size phenotype can be described as being flanked by:

a) loci NW0248118 (SEQ ID NO: 1) and NW0251236 (SEQ ID NO: 2);
b) loci NW0248118 (SEQ ID NO: 1) and NW0250242 (SEQ ID NO: 3);
c) loci NW0248118 (SEQ ID NO: 1) and NW0248583 (SEQ ID NO: 4);
d) loci NW0251236 (SEQ ID NO: 2) and NW0250242 (SEQ ID NO: 3);
e) loci NW0251236 (SEQ ID NO: 2) and NW0248583 (SEQ ID NO: 4); or
f) loci NW0250242 (SEQ ID NO: 3) and NW0248583 (SEQ ID NO: 4).

Certain of the various embodiments of the present disclosure utilize a QTL or polymorphic nucleic acid marker or allele located in one or more of these regions or subregions on LG2.

LG4

One genomic region associated with a desired seed size phenotype is located at watermelon linkage group 4 and, on the genetic map of the KBS×NHM population, flanked by loci NW0249249 (SEQ ID NO: 9) and NW0249873 (SEQ ID NO: 11).

A major watermelon seed size QTL was found to be located within this region. Certain of the various embodiments of the present disclosure utilize a QTL or polymorphic nucleic acid marker or allele located in this genomic region. Flanking markers that identify a genomic region associated with a desired seed size phenotype include loci NW0249249 (SEQ ID NO: 9) and NW0249873 (SEQ ID NO: 11). Intervening markers on LG4 that identify a genomic region associated with a desired seed size phenotype include NW0250697 (SEQ ID NO: 10). This genomic region, or subregions thereof, associated with a desired seed size phenotype can be described as being flanked by:

a) loci NW0249249 (SEQ ID NO: 9) and NW0250697 (SEQ ID NO: 10);
b) loci NW0249249 (SEQ ID NO: 9) and NW0249873 (SEQ ID NO: 11); or
c) loci NW0250697 (SEQ ID NO: 10) and NW0249873 (SEQ ID NO: 11).

Certain of the various embodiments of the present disclosure utilize a QTL or polymorphic nucleic acid marker or allele located in one or more of these regions or subregions on LG4.

LG9

One genomic region associated with a desired seed size phenotype is located at watermelon linkage group 9 and, on the genetic map of the KBS×NHM population, flanked by loci NW0250227 (SEQ ID NO: 12) and NW0249226 (SEQ ID NO: 15); and on the genetic map of the ZWRM× *Citroides* population, flanked by loci NW0249185 (SEQ ID NO: 14) and NW0249974 (SEQ ID NO: 18). Loci NW0249185 (SEQ ID NO: 14) was identified in both the KBS×NHM population and the ZWRM×*Citroides* population. It is noted that marker order and distances between markers for the consensus map was calculated based on common markers between maps, rather than recombination frequencies (see e.g., Example 3, Example 4, FIG. 3).

A major watermelon seed size QTL was found to be located within this region. Certain of the various embodiments of the present disclosure utilize a QTL or polymorphic nucleic acid marker or allele located in this genomic region. Flanking markers on LG9 that identify a genomic region associated with a desired seed size phenotype include loci NW0250227 (SEQ ID NO: 12) and NW0249974 (SEQ ID NO: 18). Intervening markers on LG9 that identify a genomic region associated with a desired seed size phenotype include Loci on LG9 associated with desired seed size phenotype included NW0250857 (SEQ ID NO: 13); NW0249185 (SEQ ID NO: 14); NW0249226 (SEQ ID NO: 15); NW0248254 (SEQ ID NO: 16); and NW0249883 (SEQ ID NO: 17); (see e.g., FIG. 3). This genomic region, or subregions thereof, associated with a desired seed size phenotype can be described as being flanked by:

a) loci NW0250227 (SEQ ID NO: 12) and NW0250857 (SEQ ID NO: 13);
b) loci NW0250227 (SEQ ID NO: 12) and NW0249185 (SEQ ID NO: 14);
c) loci NW0250227 (SEQ ID NO: 12) and NW0249226 (SEQ ID NO: 15);
d) loci NW0250227 (SEQ ID NO: 12) and NW0248254 (SEQ ID NO: 16);
e) loci NW0250227 (SEQ ID NO: 12) and NW0249883 (SEQ ID NO: 17);
f) loci NW0250227 (SEQ ID NO: 12) and NW0249974 (SEQ ID NO: 18);
g) loci NW0250857 (SEQ ID NO: 13) and NW0249185 (SEQ ID NO: 14);
h) loci NW0250857 (SEQ ID NO: 13) and NW0249226 (SEQ ID NO: 15);
i) loci NW0250857 (SEQ ID NO: 13) and NW0248254 (SEQ ID NO: 16);
j) loci NW0250857 (SEQ ID NO: 13) and NW0249883 (SEQ ID NO: 17);
k) loci NW0250857 (SEQ ID NO: 13) and NW0249974 (SEQ ID NO: 18);
l) loci NW0249185 (SEQ ID NO: 14) and NW0249226 (SEQ ID NO: 15);
m) loci NW0249185 (SEQ ID NO: 14) and NW0248254 (SEQ ID NO: 16);
n) loci NW0249185 (SEQ ID NO: 14) and NW0249883 (SEQ ID NO: 17);
o) loci NW0249185 (SEQ ID NO: 14) and NW0249974 (SEQ ID NO: 18);
p) loci NW0249226 (SEQ ID NO: 15) and NW0248254 (SEQ ID NO: 16);
q) loci NW0249226 (SEQ ID NO: 15) and NW0248254 (SEQ ID NO: 16);
r) loci NW0249226 (SEQ ID NO: 15) and NW0248254 (SEQ ID NO: 16);
s) loci NW0248254 (SEQ ID NO: 16) and NW0249883 (SEQ ID NO: 17);
t) loci NW0248254 (SEQ ID NO: 16) and NW0249974 (SEQ ID NO: 18); or
u) loci NW0249883 (SEQ ID NO: 17) and NW0249974 (SEQ ID NO: 18).

Certain of the various embodiments of the present disclosure utilize a QTL or polymorphic nucleic acid marker or allele located in one or more of these regions or subregions on LG9.

LG11

One genomic region associated with a desired seed size phenotype is located at watermelon linkage group 11 and, on the genetic map of the ZWRM×*Citroides* population, flanked by loci NW0248282 (SEQ ID NO: 19) and NW0250036 (SEQ ID NO: 22).

A major watermelon seed size QTL was found to be located within this region. Certain of the various embodiments of the present disclosure utilize a QTL or polymorphic nucleic acid marker or allele located in this genomic region. Flanking markers that identify a genomic region associated with a desired seed size phenotype include loci NW0248282 (SEQ ID NO: 19) and NW0250036 (SEQ ID NO: 22). Intervening markers on LG11 that identify a genomic region associated with a desired seed size phenotype include NW0249891 (SEQ ID NO: 20) and NW0251129 (SEQ ID NO: 21). This genomic region, or subregions thereof, associated with a desired seed size phenotype can be described as being flanked by:

a) loci NW0248282 (SEQ ID NO: 19) and NW0249891 (SEQ ID NO: 20);
b) loci NW0248282 (SEQ ID NO: 19) and NW0251129 (SEQ ID NO: 21);
c) loci NW0248282 (SEQ ID NO: 19) and NW0250036 (SEQ ID NO: 22);
d) loci NW0249891 (SEQ ID NO: 20) and NW0251129 (SEQ ID NO: 21);
e) loci NW0249891 (SEQ ID NO: 20) and NW0250036 (SEQ ID NO: 22); or
f) loci NW0251129 (SEQ ID NO: 21) and NW0250036 (SEQ ID NO: 22).

Certain of the various embodiments of the present disclosure utilize a QTL or polymorphic nucleic acid marker or allele located in one or more of these regions or subregions on LG11.

The above markers and allelic states are exemplary. One of skill in the art would recognize how to identify watermelon plants with other polymorphic nucleic acid markers and allelic states thereof related to watermelon seed size consistent with the present disclosure. One of skill the art would also know how to identify the allelic state of other polymorphic nucleic acid markers located in the genomic region(s) or linked to the QTL or other markers identified herein, to determine their association with watermelon seed size.

Watermelons are natural diploids, having their chromosomes arranged in pairs. Watermelon plants, however, can undergo a duplication of their entire set of chromosomes and exist as tetraploids. While it is uncommon for watermelons to produce spontaneous tetraploids, this process can be routinely produced in the laboratory using cell biology techniques. Triploid seeds can be produced by crossing a tetraploid parent by a diploid parent. When triploid plants are grown, seed formation in the fruit aborts because of the ploidy level differences, resulting in seedless fruits.

In certain embodiments of methods of the invention, a diploid parent plant is homozygous for the QTL or a polymorphic nucleic acid marker allele associated with the desired seed size phenotype. The diploid parent is crossed with a tetraploid lacking the QTL or a polymorphic nucleic acid marker allele associated with the desired seed size phenotype, to produce triploid hybrid progeny. This results in one copy of the QTL or polymorphic marker allele associated with the desired seed size phenotype (from the diploid parent) and two non-QTL/marker alleles (from the tetraploid parent) in the triploid hybrid. Alternatively, in certain embodiments of methods of the invention, a tetraploid parent plant is homozygous for the QTL or a polymorphic nucleic acid marker allele associated with the desired seed size phenotype. The tetraploid parent is crossed with a diploid lacking the QTL or a polymorphic nucleic acid marker allele associated with the desired seed size phenotype, to produce triploid hybrid progeny. This results in two copies of the QTL or polymorphic marker allele associated with the desired seed size phenotype (from the tetraploid parent) and one non-QTL/marker allele (from the diploid parent) in the triploid hybrid.

Certain embodiments of the invention contemplate the use of dihaploidization to produce an inbred line. A haploid plant has only one copy of each chromosome instead of the normal pair of chromosomes in a diploid plant. Haploid plants can be produced, for example, by treating with a haploid inducer. Haploid plants can be subjected to treatment that causes the single copy chromosome set to double, producing a duplicate copy of the original set. The resulting plant is termed a "double-haploid" and contains pairs of chromosomes that are generally in a homozygous allelic state at any given locus. Dihaploidization can reduce the time required to develop new inbred lines in comparison to developing lines through successive rounds of backcrossing.

One of skill in the art would understand that polymorphic nucleic acids that are located in the genomic regions identified may be used in certain embodiments of the methods of the invention. Given the provisions herein of a genomic region, QTL, and polymorphic markers identified herein, additional markers located either within or near a genomic region described herein that are associated with the phenotype can be obtained by typing new markers in various germplasm. The genomic region, QTL, and polymorphic markers identified herein can also be mapped relative to any publicly available physical or genetic map to place the region described herein on such map. One of skill in the art would also understand that additional polymorphic nucleic acids that are genetically linked to the QTL associated with a desired seed size phenotype and that map within 40 cM, 20 cM, 10 cM, 5 cM, or 1 cM of the QTL or the markers associated with a desired seed size phenotype may also be used.

V. Introgression of a Genomic Locus Associated with a Desired Seed Size Phenotype Provided herein are unique watermelon germplasms or watermelon plants comprising an introgressed genomic region that is associated with a desired seed size phenotype and method of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (e.g., desired seed size phenotype germplasm) and both linked and unlinked markers characteristic of the desired genetic background of a second germplasm.

Flanking markers that identify a genomic region associated with a desired seed size phenotype can include any loci described above on LG2, LG4, LG9, or LG11; and those that identify sub-regions thereof include can include any loci or loci intervals described above on LG2, LG4, LG9, or LG11.

For example, flanking markers that identify a genomic region or subregion include those defined by loci NW0248118 (SEQ ID NO: 1) and NW0248583 (SEQ ID NO: 4) on linkage group 2 (LG2), or within 15 cM thereof; loci NW0251236 (SEQ ID NO: 2) and NW0250242 (SEQ ID NO: 3) on linkage group 2 (LG2), or within 15 cM thereof; loci NW0251455 (SEQ ID NO: 5) and NW0248118 (SEQ ID NO: 1) on linkage group 2 (LG2), or within 15 cM thereof; loci NW0249249 (SEQ ID NO: 9) and NW0249873 (SEQ ID NO: 11) on linkage group 4 (LG4), or within 15 cM thereof; loci NW0250227 (SEQ ID NO: 12) and NW0249974 (SEQ ID NO: 18) on linkage group 9 (LG9), or within 15 cM thereof; or loci NW0248282 (SEQ ID NO: 19) and NW0250036 (SEQ ID NO: 22) on linkage group 11 (LG11), or within 15 cM thereof.

In further embodiments, markers are provided in a genomic region flanked by loci NW0251455 (SEQ ID NO: 5) and NW0249783 (SEQ ID NO: 6) on LG2; loci NW0249783 (SEQ ID NO: 6) and NW0250500 (SEQ ID NO: 7) on LG2; loci NW0250500 (SEQ ID NO: 7) and NW0250854 (SEQ ID NO: 8) on LG2; loci NW0250854 (SEQ ID NO: 8) and NW0248118 (SEQ ID NO: 1) on LG2; loci NW0248118 (SEQ ID NO: 1) and NW0251236 (SEQ ID NO: 2) on LG2; loci NW0248118 (SEQ ID NO: 1) and NW0250242 (SEQ ID NO: 3) on LG2; loci NW0248118 (SEQ ID NO: 1) and NW0248583 (SEQ ID NO: 4) on LG2; loci NW0251236 (SEQ ID NO: 2) and NW0250242 (SEQ ID NO: 3) on LG2; loci NW0251236 (SEQ ID NO: 2) and NW0248583 (SEQ ID NO: 4) on LG2; loci NW0250242 (SEQ ID NO: 3) and NW0248583 (SEQ ID NO: 4) on LG2; loci NW0249249 (SEQ ID NO: 9) and NW0250697 (SEQ ID NO: 10) on LG4; loci NW0249249 (SEQ ID NO: 9) and NW0249873 (SEQ ID NO: 11) on LG4; loci NW0250697 (SEQ ID NO: 10) and NW0249873 (SEQ ID NO: 11) on LG4; loci NW0250227 (SEQ ID NO: 12) and NW0250857 (SEQ ID NO: 13) on LG9; loci NW0250227 (SEQ ID NO: 12) and NW0249185 (SEQ ID NO: 14) on LG9; loci NW0250227 (SEQ ID NO: 12) and NW0249226 (SEQ ID NO: 15) on LG9; loci NW0250227 (SEQ ID NO: 12) and NW0248254 (SEQ ID NO: 16) on LG9; loci NW0250227 (SEQ ID NO: 12) and NW0249883 (SEQ ID NO: 17) on LG9; loci NW0250227 (SEQ ID NO: 12) and NW0249974 (SEQ ID NO: 18) on LG9; loci NW0250857 (SEQ ID NO: 13) and NW0249185 (SEQ ID NO: 14) on LG9; loci NW0250857 (SEQ ID NO: 13) and NW0249226 (SEQ ID NO: 15) on LG9; loci NW0250857 (SEQ ID NO: 13) and NW0248254 (SEQ ID NO: 16) on LG9; loci NW0250857 (SEQ ID NO: 13) and NW0249883 (SEQ ID NO: 17) on LG9; loci NW0250857 (SEQ ID NO: 13) and NW0249974 (SEQ ID NO: 18) on LG9; loci NW0249185 (SEQ ID NO: 14) and NW0249226 (SEQ ID NO: 15) on LG9; loci NW0249185 (SEQ ID NO: 14) and NW0248254 (SEQ ID NO: 16) on LG9; loci NW0249185 (SEQ ID NO: 14) and NW0249883 (SEQ ID NO: 17) on LG9; loci NW0249185 (SEQ ID NO: 14) and NW0249974 (SEQ ID NO: 18) on LG9; loci NW0249226 (SEQ ID NO: 15) and NW0248254 (SEQ ID NO: 16) on LG9; loci NW0248254 (SEQ ID NO: 16) and NW0249883 (SEQ ID NO: 17) on LG9; loci NW0248254 (SEQ ID NO: 16) and NW0249974 (SEQ ID NO: 18) on LG9; loci NW0249883 (SEQ ID NO: 17) and NW0249974 (SEQ ID NO: 18) on LG9; loci NW0248282 (SEQ ID NO: 19) and NW0249891 (SEQ ID NO: 20) on LG11; loci NW0248282 (SEQ ID NO: 19) and NW0251129 (SEQ ID NO: 21) on LG11; loci NW0248282 (SEQ ID NO: 19) and NW0250036 (SEQ ID NO: 22) on LG11; loci NW0249891 (SEQ ID NO: 20) and NW0251129 (SEQ ID NO: 21) on LG11; loci NW0249891 (SEQ ID NO: 20) and NW0250036 (SEQ ID NO: 22) on LG11; or loci NW0251129 (SEQ ID NO: 21) and NW0250036 (SEQ ID NO: 22) on LG11; or within 15 cM thereof.

Flanking markers that fall on both the telomere proximal end and the centromere proximal end of any of these genomic intervals may be useful in a variety of breeding efforts that include, but are not limited to, introgression of genomic regions associated with a desired seed size phenotype into a genetic background comprising markers associated with germplasm that ordinarily contains a genotype associated with another phenotype.

Markers that are linked and either immediately adjacent or adjacent to the identified desired seed size phenotype QTL that permit introgression of the QTL in the absence of extraneous linked DNA from the source germplasm containing the QTL are provided herewith. Those of skill in the art will appreciate that when seeking to introgress a smaller genomic region comprising a QTL associated with a desired seed size phenotype described herein, that any of the telomere proximal or centromere proximal markers that are immediately adjacent to a larger genomic region comprising the QTL can be used to introgress that smaller genomic region.

A marker within about 40 cM of a marker of a seed size phenotype QTL described herein may be useful in a variety of breeding efforts that include, but are not limited to, introgression of genomic regions associated with a desired seed size phenotype into a genetic background comprising markers associated with germplasm that ordinarily contains a genotype associated with another phenotype. For example, a marker within 40 cM, 20 cM, 15 cM, 10 cM, 5 cM, 2 cM, or 1 cM of a seed size phenotype QTL or marker described herein can be used for marker-assisted introgression of a desired seed size phenotype.

A marker within about 40 cM of a seed size phenotype QTL marker on LG2 described herein can be used for marker-assisted introgression of a desired seed size phenotype. For example, a marker within 40 cM, 20 cM, 15 cM, 10 cM, 5 cM, 2 cM, or 1 cM of a seed size phenotype QTL marker on LG2 described herein can be used for marker-assisted introgression of a desired seed size phenotype. As described above, a seed size phenotype QTL marker on LG2 can include one or more of NW0248118 (SEQ ID NO: 1); NW0251236 (SEQ ID NO: 2); NW0250242 (SEQ ID NO: 3); or NW0248583 (SEQ ID NO: 4).

A marker within about 40 cM of a seed size phenotype QTL marker on LG4 described herein can be used for marker-assisted introgression of a desired seed size phenotype. For example, a marker within 40 cM, 20 cM, 15 cM, 10 cM, 5 cM, 2 cM, or 1 cM of a seed size phenotype QTL marker on LG4 described herein can be used for marker-assisted introgression of a desired seed size phenotype. As described above, a seed size phenotype QTL marker on LG4 can include one or more of NW0249249 (SEQ ID NO: 9); NW0250697 (SEQ ID NO: 10); or NW0249873 (SEQ ID NO: 11).

A marker within about 40 cM of a seed size phenotype QTL marker on LG9 described herein can be used for marker-assisted introgression of a desired seed size phenotype. For example, a marker within 40 cM, 20 cM, 15 cM, 10 cM, 5 cM, 2 cM, or 1 cM of a seed size phenotype QTL marker on LG9 described herein can be used for marker-assisted introgression of a desired seed size phenotype. As described above, a seed size phenotype QTL marker on LG9 can include one or more of NW0250227 (SEQ ID NO: 12); NW0250857 (SEQ ID NO: 13); NW0249185 (SEQ ID NO: 14); NW0249226 (SEQ ID NO: 15); NW0248254 (SEQ ID NO: 16); NW0249883 (SEQ ID NO: 17); or NW0249974 (SEQ ID NO: 18).

A marker within about 40 cM of a seed size phenotype QTL marker on LG11 described herein can be used for marker-assisted introgression of a desired seed size phenotype. For example, a marker within 40 cM, 20 cM, 15 cM, 10 cM, 5 cM, 2 cM, or 1 cM of a seed size phenotype QTL marker on LG11 described herein can be used for marker-assisted introgression of a desired seed size phenotype. As described above, a seed size phenotype QTL marker on LG11 can include one or more of NW0248282 (SEQ ID NO: 19); NW0249891 (SEQ ID NO: 20); NW0251129 (SEQ ID NO: 21); or NW0250036 (SEQ ID NO: 22).

Watermelon plants or germplasm comprising an introgressed region that is associated with a desired seed size phenotype wherein at least 10%, 25%, 50%, 75%, 90%, or 99% of the remaining genomic sequences carry markers characteristic of plant or germplasm that otherwise or ordinarily comprise a genomic region associated with another phenotype, are thus provided. Furthermore, watermelon plants comprising an introgressed region where closely linked regions adjacent and/or immediately adjacent to the genomic regions, QTL, and markers provided herewith that comprise genomic sequences carrying markers characteristic of watermelon plants or germplasm that otherwise or ordinarily comprise a genomic region associated with the phenotype are also provided.

VI. Molecular Assisted Breeding Techniques

Genetic markers that can be used in the practice of the present invention include, but are not limited to, Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Recently, single nucleotide polymorphism (SNP) genetic maps were produced using diverse *C. lanatus* parents, including a population produced from an elite×elite (*C. lanatus* var. *lanatus*) cross and a population from an intersubspecific cross between an elite cultivar and *C. lanatus* var. *citroides*. As described herein, genetically diverse mapping populations that segregate for seed size were used to identify main effect QTL (M-QTL) and epistatic QTL (E-QTL) associated with seed size in watermelon. Results described herein identify main and epistatic QTL on LG2, LG4, and LG9 that can control seed size in watermelon. As described further herein, the M-QTL on LG 2 can be a target for marker assisted selection of seed size in watermelon breeding programs.

As a set, polymorphic markers serve as a useful tool for fingerprinting plants to inform the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a watermelon plant a genotype associated with a desired seed size phenotype, identify a watermelon plant with a genotype associated with desired seed size phenotype, and to select a watermelon plant with a genotype associated with a desired seed size phenotype. In certain embodiments of methods of the invention, polymorphic nucleic acids can be used to produce a watermelon plant that comprises in its genome an introgressed locus associated with a desired seed size phenotype. In certain embodiments of the invention, polymorphic nucleic acids can be used to breed progeny watermelon plants comprising a locus associated with a desired seed size phenotype.

Certain genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

A number of different marker types are available for use in genetic mapping. Exemplary genetic marker types include, but are not limited to, restriction fragment length polymorphisms (RFLPs), simple sequence length polymorphisms (SSLPs), amplified fragment length polymorphisms (AFLPs), single nucleotide polymorphisms (SNPs), nucleotide insertions and/or deletions (INDELs) and isozymes. Polymorphisms comprising as little as a single nucleotide change can be assayed in a number of ways. For example, detection can be made by electrophoretic techniques including a single strand conformational polymorphism (Orita et al. (1989) Genomics, 8(2), 271-278), denaturing gradient gel electrophoresis (Myers (1985) EPO 0273085), or cleavage fragment length polymorphisms (Life Technologies, Inc., Gathersberg, Md. 20877), but the widespread availability of DNA sequencing machines often makes it easier to just sequence amplified products directly. Once the polymorphic sequence difference is known, rapid assays can be designed for progeny testing, typically involving some version of PCR amplification of specific alleles (PASA, Sommer, et al. (1992) Biotechniques 12(1), 82-87), or PCR amplification of multiple specific alleles (PAMSA, Dutton and Sommer (1991) Biotechniques, 11(6), 700-7002).

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with a desired seed size phenotype.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800, 944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996, 476.

Target nucleic acid sequence can also be detected by probe linking methods as disclosed in U.S. Pat. No. 5,616, 464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R. F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs.

EXAMPLES

The following disclosed embodiments are merely representative of the invention which may be embodied in various forms. Thus, specific structural, functional, and procedural details disclosed in the following examples are not to be interpreted as limiting.

Example 1: Plant Materials and Genetic Maps

Figure 1B:
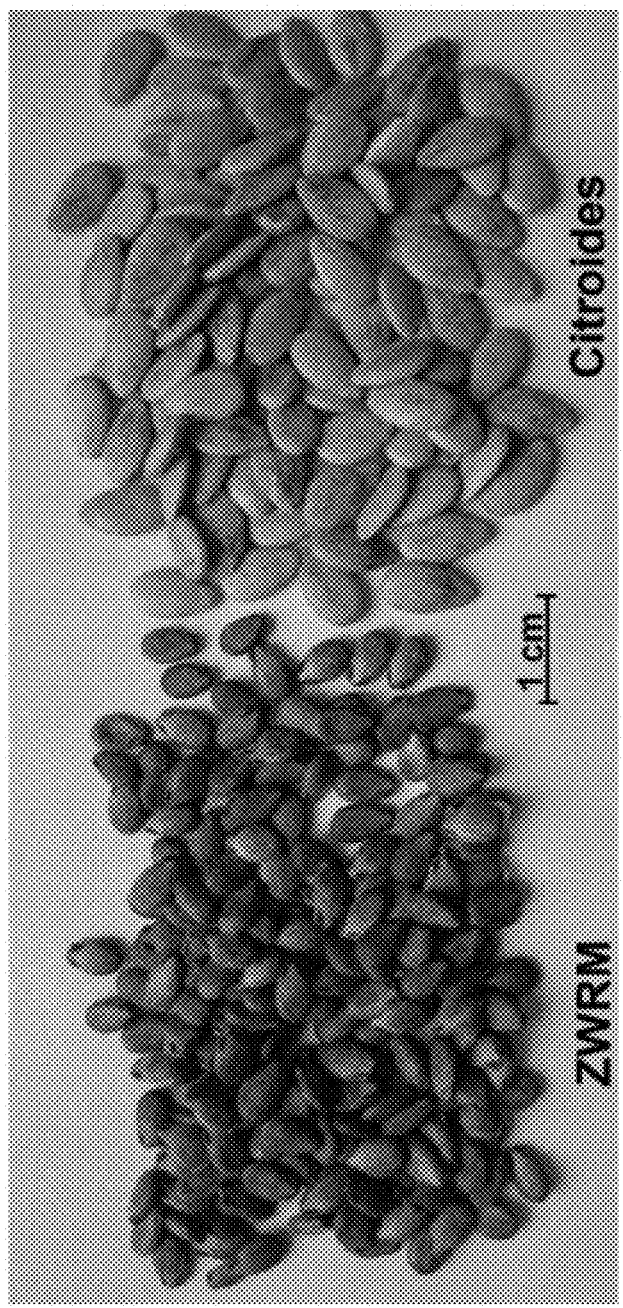

The development of the mapping populations and creation of the genetic maps have been described previously. Briefly, a recombinant inbred line population (RIL, $F_6$) was developed by single seed descent from a cross between the elite cultivars (*C. lanatus* var. *lanatus*) Klondike Black Seeded (KBS; PI 635609) and New Hampshire Midget (NHM; PI 635617) and an $F_2$ population was created from a cross between an elite cultivar from China (ZWRM50; PI 593359) and a wild *C. lanatus* var. *citroides* accession from South Africa (*Citroides*; PI 244019). The weight of 100 seeds (100SWT) for KBS, NHM, ZWRM50 and *Citroides* were 4.96 g, 6.68 g, 2.00 g and 5.44 g, respectively. The average seed length (SL) of 10 randomly chosen seed of each parent were 8.38 mm, 10.67 mm, 6.16 mm and 8.59 mm, while the seed width (SWD) were 5.30 mm, 6.55 mm, 3.69 mm and 5.01 mm (FIG. 1).

SNP markers were developed for *C. lanatus* and used to create genetic maps with 378 markers for the KBS×NHM population and 338 markers for the ZWRM×*Citroides* population.

Example 2: Trait Phenotyping

A single plant for each KBS×NHM $F_6$ RIL line and individual ZWRM×*Citroides* $F_2$ plants were grown in a greenhouse at different times. For both populations seed were germinated in seedling trays and transplanted 4 weeks later into 14.136-L Blow Molded pots (Product number C1600, Nursery Supplies Inc. Kissimmee, Fla.) filled with Fafard 3B mix (Conrad Fafard, Inc., Agawam, Mass.) and 12 g Osmocote (14N-4.2P-11.6K; Scotts Miracle-Gro, Marysville, Ohio) per pot.

The seed were harvested by hand and allowed to dry before measurements were taken for 100SWT in grams, and SL and SWD in millimeters, measured with a digital caliper (Balkamp Manufacturing Corp., Indianapolis, Ind.). The SL and SWD values used for QTL mapping were the average measurements of five random seeds per fruit.

Example 3: QTL Detection

Analysis for the detection of M-QTL was performed using WinQTL Cartographer (WinQTL Cart) version 2.5 (Wang, S., C. J. Basten, and Z. B. Zeng. 2011. Windows QTL Cartographer 2.5, Department of Statistics, North Carolina State University, Raleigh, N.C.). All data were analyzed by composite interval mapping (CIM) (Zeng, Z. B. 1993. Theoretical basis of separation of multiple linked gene effects on mapping quantitative trait loci. Proceedings of the National Acadamy of Sciences USA 90:10972-10976; Zeng, Z. B. 1994. Precision mapping of quantitative trait loci. Genetics 136:1457-1468) using permutation tests (1,000 permutations, $\alpha$=0.05) to determine the threshold values for each trait (Churchill, G. A. and R. W. Doerge. 1994. Empirical threshold values for quantitative trait mapping. Genetics. 138:963-971; Doerge, R. W. and G. A. Churchill. 1996. Permutation tests for multiple loci affecting a quantitative character. Genet. Mol. Biol. 142:285-294). CIM analysis was performed using the standard model (Model 6) with a walk speed of 1 cM and forward-backward stepwise regression to set the number of marker cofactors. The cofactors within 10 cM on either side of the QTL were excluded from the model. QTL identified on the same linkage group (LG) were considered separate QTL if they were separated by at least 20 cM (Ravi, K., V. Vadez, S. Isobe, R. Mir, Y. Guo, S. Nigam, M. Gowda, T. Radhakrishnan, D. Bertioli, S. Knapp, and R. Varshney. 2011. Identification of several small main-effect QTLs and a large number of epistatic QTLs for drought tolerance related traits in groundnut (*Arachis hypogaea* L.). Theor. Appl. Genet. 122:1119-1132). QTL were considered minor, intermediate and major if $R^2$ was less than 10%, between 10% and 25% and more than 25% respectively.

Analysis for epistatic interaction between M-QTL was carried out using multiple interval mapping (MIM) (Kao, C.-H. and Z.-B. Zeng. 1997. General formulas for obtaining the MLEs and the asymptotic variance-covariance matrix in mapping quantitative trait loci when using the EM algorithm. Biometrics 53: 653-665; Kao, C.-H., Z.-B. Zeng, and R. D. Teasdale. 1999. Multiple interval mapping for quantitative trait loci. Genetics 152:1203-1216; Zeng Zeng, Z. B., C. H. Kao, and C. J. Basten. 1999. Estimating the genetic architecture of quantitative traits. Genet Research 74:279-289) in WinQTL Cart version 2.5 (Wang et al., 2011). Significance was determined as recommended by the authors using the information criteria IC(k)=-2(log(L)-kc(n)/2) and penalty function c(n)=log(n).

Example 4: Identification of QTL

Methods are according to Examples 1-3 unless described otherwise.

Correlations between the three seed traits were statistically significant and high in both populations, but somewhat higher in the ZWRM×*Citroides* populations than in the KBS×NHM population (Table 1). Transgressive segregation was observed for all three traits (FIG. 2) suggesting the involvement of antagonistic additive effects (deVicente, M. C. and S. D. Tanksley. 1993. QTL analysis of transgressive segregation in an interspecific tomato cross. Genetics 134: 585-596; Rieseberg, L. H., M. A. Archer, and R. K. Wayne. 1999. Transgressive segregation, adaptation and speciation. Heredity 83:363-372).

Table 1: Pearson correlations for 100 seed weight (100SWT), seed length (SL) and seed width (SWD) in the (TABLE 1A) Klondike Black Seeded×New Hampshire Midget (KBS×NHM) and (TABLE 1B) ZWRM50×PI 244019 (ZWRM×*Citroides*) populations. Starred numbers (*) indicate significant (P<0.001) correlations.

TABLE 1A

| KBS × NHM | 100SWT | SL |
|---|---|---|
| SL | 0.88* | |
| SWD | 0.86* | 0.93* |

TABLE 1B

| ZWRM × Citroides | 100SWT | SL |
|---|---|---|
| SL | 0.95* | |
| SWD | 0.96* | 0.97* |

A total of 13 QTL were identified in the two populations for the three traits (Table 2, FIG. 3). In the KBS×NHM populations three, two and one QTL were detected for 100SWT, SL and SWD respectively, while two (100SWT), three (SL) and two (SWD) were identified in the ZWRM× *Citroides* population.

TABLE 2

Genomic regions associated with QTL for 100 seed weight (100SWT), seed length (SL) and seed width (SWD) in the Klondike Black Seeded × New Hampshire Midget (KBS × NHM) and ZWRM50 × PI 244019 (ZWRM × Citroides) populations.

| Trait | Population | LG | Suggested QTL name | Left Marker | Position (cM) | LOD | $R^2$ (%) | Additive effect | Dominance effect | LOD-1 support interval (cM) | LOD-1 support interval (cM) |
|---|---|---|---|---|---|---|---|---|---|---|---|
| 100SWT | KBS × NHM | 2 | swt2.1 | NW0251236 (SEQ ID NO: 2) | 0.0 | 13.5 | 26.9 | −1.371 | . | 0.0 | 2.0 |
| | KBS × NHM | 4 | swt4.1 | NW0250697 (SEQ ID NO: 10) | 48.6 | 5.0 | 7.9 | 0.738 | . | 48.2 | 50.4 |
| | KBS × NHM | 9 | swt9.1 | NW0250857 (SEQ ID NO: 13) | 66.3 | 3.1 | 4.8 | 0.583 | . | 62.2 | 70.6 |
| | ZWRM × Citroides | 2 | swt2.1 | NW0248118 (SEQ ID NO: 1) | 23.1 | 37.6 | 73.6 | −3.523 | −2.949 | 22.8 | 25.7 |
| | ZWRM × Citroides | 9 | swt9.1 | NW0248796 | 115.1 | 10.2 | 16.0 | 0.971 | 2.143 | 105.6 | 119.4 |
| SL | KBS × NHM | 2 | sl2.1 | NW0251236 (SEQ ID NO: 2) | 0.0 | 21.1 | 41.3 | −1.065 | . | 0.0 | 2.1 |
| | KBS × NHM | 4 | sl4.1 | NW0250697 (SEQ ID NO: 10) | 48.6 | 4.0 | 5.3 | 0.379 | . | 36.8 | 50.6 |

TABLE 2-continued

Genomic regions associated with QTL for 100 seed weight (100SWT), seed length (SL) and seed width (SWD) in the Klondike Black Seeded × New Hampshire Midget (KBS × NHM) and ZWRM50 × PI 244019 (ZWRM × Citroides) populations.

| Trait | Population | LG | Suggested QTL name | Left Marker | Position (cM) | LOD | $R^2$ (%) | Additive effect | Dominance effect | LOD-1 support interval (cM) | LOD-1 support interval (cM) |
|---|---|---|---|---|---|---|---|---|---|---|---|
| | ZWRM × Citroides | 2 | sl2.1 | NW0248118 (SEQ ID NO: 1) | 22.1 | 39.6 | 69.2 | −2.272 | −1.775 | 21.8 | 25.4 |
| | ZWRM × Citroides | 9 | sl9.1 | NW0248796 | 114.1 | 16.6 | 22.4 | 0.993 | 1.407 | 109.7 | 119.9 |
| | ZWRM × Citroides | 11A | sl11.1 | NW0251129 | 70.6 | 3.7 | 5.4 | 0.784 | 0.644 | 66.1 | 71.6 |
| SWD | KBS × NHM | 2 | swd2.1 | NW0251236 (SEQ ID NO: 2) | 1.0 | 15.4 | 32.8 | −0.573 | . | 0.0 | 2.4 |
| | ZWRM × Citroides | 2 | swd2.1 | NW0248118 (SEQ ID NO: 1) | 23.1 | 43.1 | 69.3 | −1.380 | −1.101 | 23.1 | 25.6 |
| | ZWRM × Citroides | 9 | swd9.1 | NW0248796 | 114.1 | 18.0 | 25.6 | 0.666 | 0.852 | 109.2 | 119.4 |

LG2

In both populations intermediate to major M-QTL were detected for 100SWT ($R^2$=26.9% and 73.6%), SL ($R^2$=41.3% and 69.2%) and SWD ($R^2$=32.8% and 69.3%) at a similar location on LG 2 (Table 2, FIG. 3). Co-localization of QTL for different traits at similar chromosomal locations may indicate a single gene with pleotropic effect, or different tightly linked genes. Fine mapping of the region can elucidate this effect, but the consistent high correlation between the traits in this and other studies suggest pleotropism (Poole et al., 1941; Zhang, X. P., B. B. Rhodes, and M. Wang. 1995. Genes controlling watermelon seed size., p. 144-147. In: Lester, G. and Dunlap, J. (eds.), Cucurbitaceae '94: Evaluation and Enhancement of Cucurbit Germplasm. ASHS Press, Alexandria, Va.).

QTL that are stable across different genetic backgrounds are highly desirable for marker assisted selection. The observation that QTL identified in a particular mapping population are not useful in populations with different genetic background has been a major limiting factor in the widespread application of MAS in breeding programs (Collard, B. C. Y. and D. J. Mackill 2008. Marker-assisted selection: an approach for precision plant breeding in the twenty-first century. Philosophical Transactions of the Royal Society B: Biological Sciences 363:557-572). While both populations were grown in the greenhouse, the stability of the M-QTL on LG 2 across years and diverse genetic backgrounds suggest broad stability. The large amount of phenotypic variation explained (26.9-73.6%) by the M-QTL on LG 2 and its stability across populations makes it the prime target for MAS for seed size.

LG4

Figure 2A:
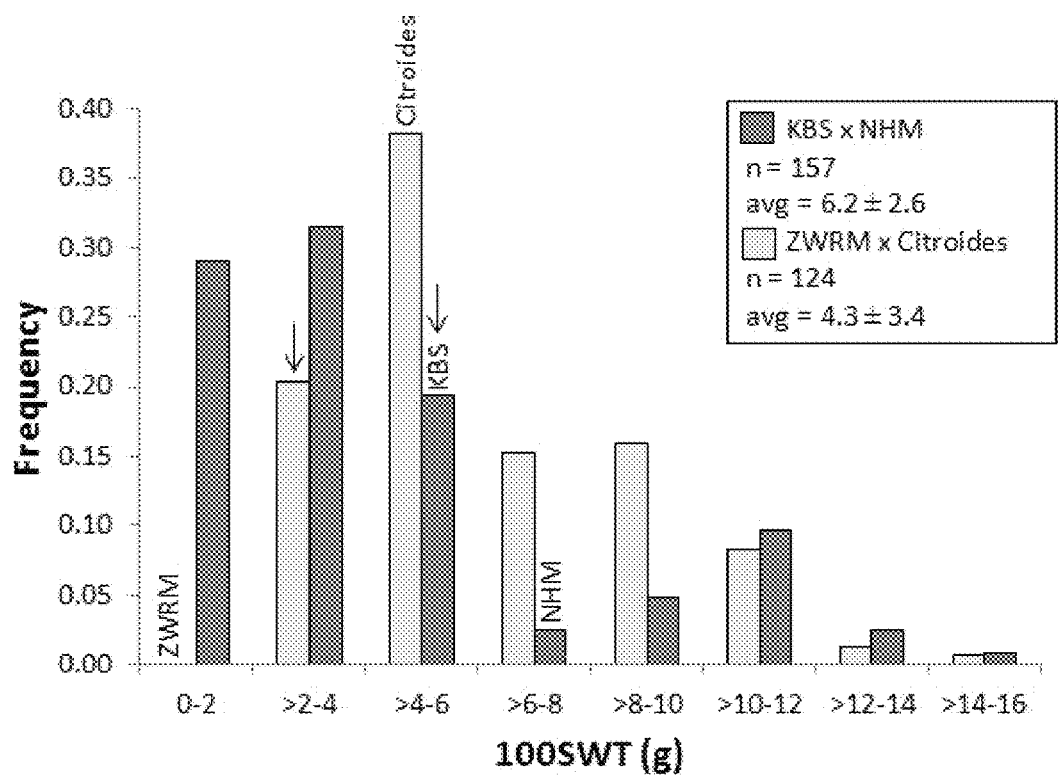
FIGS. 2A, 2B, 2C is a series of bar graphs showing frequency distribution for (FIG. 2A) 100 seed weight (100SWT) in grams (g), (FIG. 2B) seed length (SL) in millimeters (mm) and (FIG. 2C) seed width (SWD) in millimeters (mm) in the Klondike Black Seeded×New Hampshire Midget population (KBS×NHM) population and the ZWRM50×PI 244019 (ZWRM×*Citroides*) $F_2$ population as well as the parental phenotypes. Arrows indicate phenotype of $F_1$.
Figure 2B:
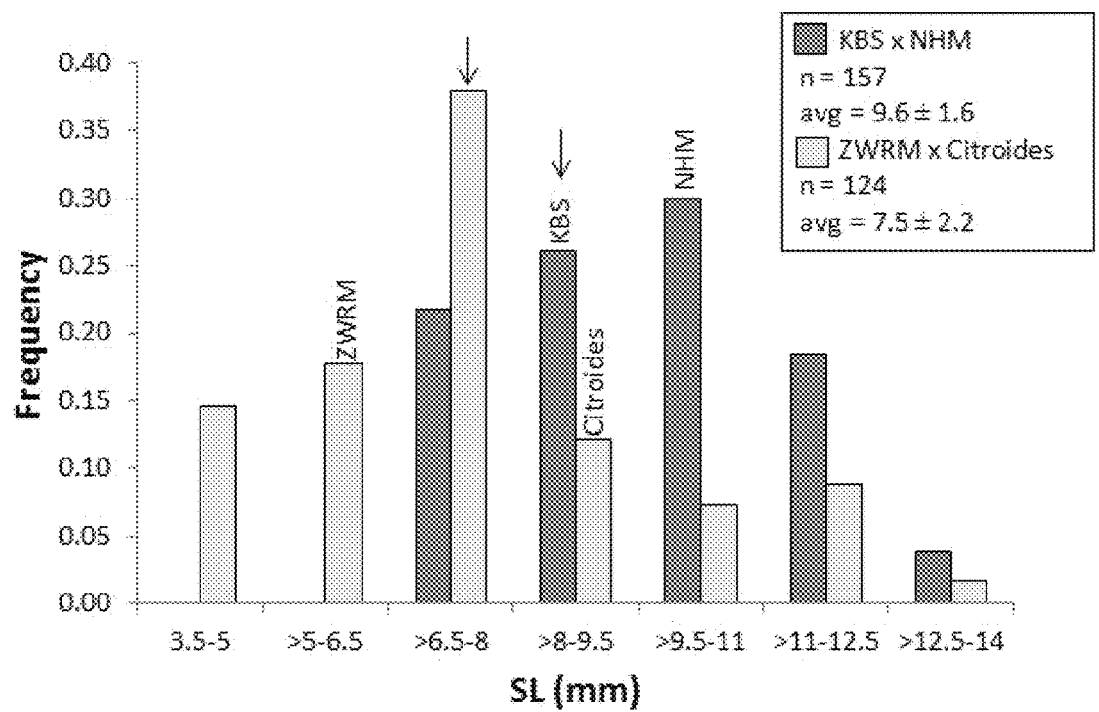
Figure 2C:
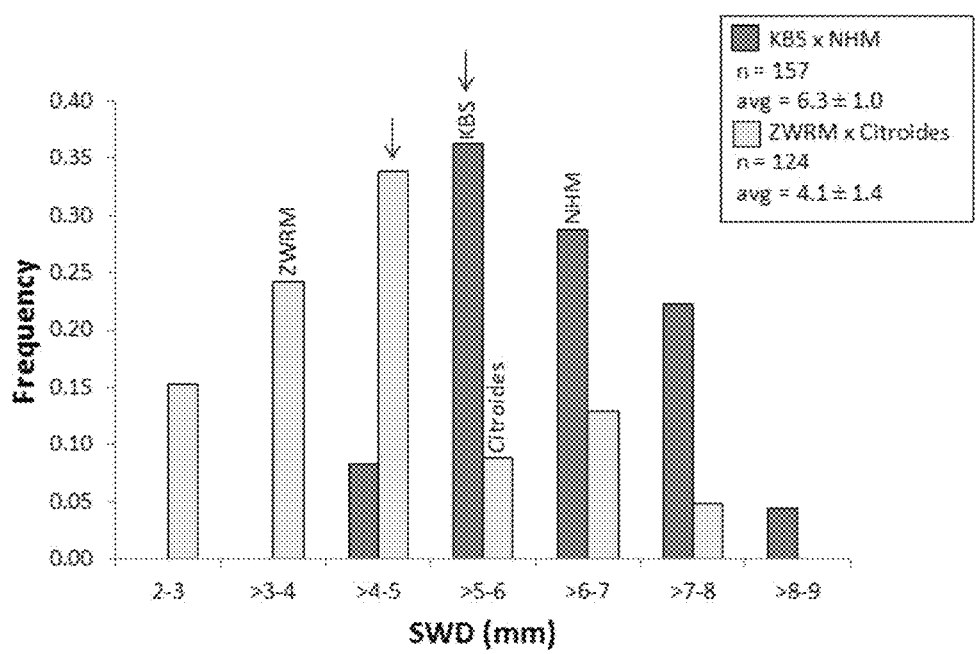

In addition to the stable M-QTL on LG 2, an additional M-QTL for 100SWT and SL were identified on LG 4 in the KBS×NHM population. This minor M-QTL had an antagonistic additive effect for these traits to the major M-QTL on LG 2, in agreement with expectations based on the observed transgressive trait segregation (FIG. 2).

The M-QTL on LG 4 was not detected in the ZWRM× Citroides population. This is, however, an inter-subspecific cross between C. lanatus var. lanatus and C. lanatus var. citroides, while the study by Poole et al., 1941 and others (Lou, L. 2009. Inheritance of Fruit Characteristics in Watermelon [Citrullus lanatus (Thunb.) Matsum. & Nakai]. North Carolina State University, Raleigh, N.C., M. S.; Tanaka, T., S. Wimol, and T. Mizutani. 1995. Inheritance of fruit shape and seed size of watermelon. J. Japan. Soc. Hort. Sci 64:543-548; Zhang, J. N. 1996. Inheritance of seed size from diverse crosses in watermelon. Cucurbit Genetics Cooperative Report 19:67-69) involved intra-subspecific crosses (similar to KBS×NHM). The population used by Hawkins et al. (2001) was similar to the ZWRM×Citroides population and assigned genes controlling SL and SWD to a single LG.

LG9

An M-QTL for 100SWT identified on LG 9 in the KBS×NHM population was located at a slightly different location on the same LG than the minor M-QTL for 100SWT, SL and SWD in the ZWRM×Citroides population. Hawkins et al. (2001) identified a RAPD marker loosely linked to SL and SWD in an intersub-specific C. lanatus population similar to the ZWRM×Citroides population. Because no markers are shared between the studies, it was not determined whether the RAPD marker might be linked to any of the M-QTL described herein.

The M-QTL identified on LG 9 is at a similar location to fruit size QTL detected in these populations. A significant correlation (r=0.20-0.27) between SL and SWD and fruit length and width was observed in the ZWRM50×Citroides population (data not shown) (Prothro, J. M. 2010. Genetic mapping of phenotypic and quantitative trait loci underlying horticulturally important traits in watermelon. University of Georgia, Athens, Ga., Masters of Science). It is possible that seed size in the results described herein was influenced by conditions in the greenhouse that can limit fruit size and further testing can show whether the QTL on LG 9 are associated with seed size under field conditions.

Epistatic Interaction

It has been suggested that there is an epistatic interaction between the genes controlling seed size in watermelon (Poole et al., 1941). MIM was used in an effort to detect such interactions in the current study. Significant epistatic interactions were detected between the M-QTL on LG 2 and LG 4 for 100SWT and SL in the KBS×NHM population, and LG 2 and LG 9 for all three traits in the ZWRM×Citroides population (Table 3, FIG. 4). The effect of the epistatic interactions is relatively small, with only the interaction between LG 2 and LG 4 for 100SWT above 5% ($R^2$=7.4%).

TABLE 3

Significant epistatic interactions between main QTL for 100 seed weight (100SWT), seed length (SL) and seed width (SWD) in the Klondike Black Seeded × New Hampshire Midget (KBS × NHM) and ZWRM50 × PI 244019 (ZWRM × Citroides) populations.

| Trait | Population | LGs | Type of Interaction[a] | Phenotypic effect | Effect (%) |
|---|---|---|---|---|---|
| 100SWT | KBS × NHM | 2 × 4 | A × A | −0.66 | 7.40% |
|  | ZWRM × Citroides | 2 × 9 | A × A | −1.31 | 1.20% |
| SL | KBS × NHM | 2 × 4 | A × A | −0.30 | 2.80% |
|  | ZWRM × Citroides | 2 × 9 | A × A | −0.36 | 1.43% |
| SWD | KBS × NHM | None |  |  |  |
|  | ZWRM × Citroides | 2 × 9 | D × A | −0.22 | 0.27% |

[a] A × A = Additive × Additive, D × A = Dominant × Additive.

Genes

It is not certain whether any of the identified M-QTL represent the s or l genes described by Poole et al. (1941). It is possible that the QTL on LG 2 and LG 4 are associated with these genes, but the absence of small seeds (~6 mm) in the KBS×NHM RIL population (FIG. 2b) suggests that the population was not segregating for the s alleles. But results described herein support that more than one gene is involved in determining seed size and that there is interaction between the genes.

Thus, results described herein identify main and epistatic QTL that control seed size in watermelon. The M-QTL on LG 2 can be a target for marker assisted selection of seed size in watermelon breeding programs.

Example 5: Validation of Seed Size QTL on LG2 in a Third Population

Bulk segregate analysis (BSA) was conducted in an F2 watermelon population segregating for small and medium seed size. In watermelon, small seed is considered dominant to medium seed, and medium seed is believed to be dominant to large, according to breeding observations. Breeders score seed size on a 1-9 scale (where 1 is tiny and 9 is large). The population used for BSA was a cross between a male inbred parent, Parent 1, (small, seed size 4) and a female inbred parent, Parent 2, (medium, seed size 6). Twenty-seven individuals were selected from the population, based on their seed size, and genotyped as individual plants. These individual plants were assigned to one of the two "bulk groups". The small seeded bulk, with seed sizes ranging from 3-4, included 10 individuals and the medium seeded bulk, with seed sizes ranging from 6-7, consisted of 17 individuals. All 27 individual plants, as well as the parental lines of the population, were fingerprinted with markers distributed across all the 12 chromosomes of watermelon.

Based on allele frequencies in the small seeded bulk vs. the medium seeded bulk the seed size QTL is likely located in proximity or within the interval of markers NW0251455 and NW0248118. Markers NW0249783, NW0250500 and NW0250854 which are in between NW0251455 and NW0248118 are also informative for the phenotype (Table 4). It should be noted that the nearest markers (NW0251236 and NW0248583) downstream of NW0248118 and the nearest marker (NW0249207) upstream of NW0251455 are not informative for this cross (Table 4). The genotype of the small seeded parent, Parent 1, was considered as the favorable allele and allele frequencies of the small and medium seeded bulks were estimated for all the informative markers on LG2 (Table 4). The frequency of the small seeded (favorable) alleles in the medium seeded bulk ranged from 0.06 to 0.12 for the informative markers on LG2 (Table 4). Furthermore, the frequency of the small seeded (favorable) alleles in the small seeded bulk ranged from 0.65 to 0.7 (Table 4). The low frequency of the favorable alleles in the medium seeded individuals and the moderately high frequency of the favorable alleles in the small seeded individuals indicated the likely position of the seed size QTL on LG2. Allelic frequencies in this experiment also suggest that NW0248118 is the most closely linked marker to the seed size QTL. Since closely linked downstream markers were not informative in this cross, and the marker NW0248118 at the edge of the interval was found to be most closely linked, it appears that this QTL may overlap with the seed size QTL identified in the other two bi-parental mapping populations discussed here, Klondike Black Seeded×New Hampshire Midget recombinant inbred lines and ZWRM50×PI 244019 $F_2$ plants.

|  |  | Marker | NW0251455 | NW0249783 | NW0250500 | NW0250854 | NW0248118 |
|---|---|---|---|---|---|---|---|
|  |  | LG | 2 | . | 2 | 2 | 2 |
|  |  | Size |  |  |  |  |  |
|  | Parent 1 | 4 | GG | CC | AA | GG | CC |
| Small seeded bulk | 1 | 3 | GG | CC | AA | GG | CC |
|  | 2 | 4 | GT | CT | AG | AG | CT |
|  | 3 | 4 | GT | CT | AG | AG | CT |
|  | 4 | 4 | TT | TT | GG | AA | CT |
|  | 5 | 4 | GT | CT | AG | AG | CT |
|  | 6 | 4 | GG | CC | AA | GG | CC |
|  | 7 | 4 | GG | CC | AA | GG | CC |
|  | 8 | 4 | GG | CC | AA | GG | CC |
|  | 9 | 4 | GT | CT | AG | AG | CT |
|  | 10 | 4 | GG | CT | AG | AG | CT |
|  | Parent 2 | 6 | TT | TT | GG | AA | TT |
| Medium seeded bulk | 1 | 6 | TT | TT | GG | AA | TT |
|  | 2 | 6 | TT | TT | GG | AA | TT |
|  | 3 | 6 | TT | TT | GG | AA | TT |
|  | 4 | 6 | GT | TT | GG | AA | TT |
|  | 5 | 6 | TT | TT | GG | AA | TT |
|  | 6 | 6 | GT | CT | AG | AG | TT |
|  | 7 | 6 | TT | CT | AG | AG | CT |
|  | 8 | 6 | TT | TT | GG | AA | TT |
|  | 9 | 6 | TT | TT | GG | AA | TT |
|  | 10 | 6 | GT | TT | GG | AA | TT |
|  | 11 | 6 | TT | TT | GG | AA | TT |

-continued

| Marker | | NW0251455 | NW0249783 | NW0250500 | NW0250854 | NW0248118 |
|---|---|---|---|---|---|---|
| 12 | 6 | TT | TT | GG | AA | TT |
| 13 | 6 | GT | CT | AG | AG | CT |
| 14 | 7 | TT | TT | GG | AA | TT |
| 15 | 7 | TT | TT | GG | AA | TT |
| 16 | 7 | TT | TT | GG | AA | TT |
| 17 | 7 | TT | TT | GG | AA | TT |
| SMALL REF genotype (Fav) | | GG | CC | AA | GG | CC |
| N (Med) with genotype | | 17 | 17 | 17 | 17 | 17 |
| N REF genotype in Med | | 0 | 0 | 0 | 0 | 0 |
| N het genotype in Med | | 4 | 3 | 3 | 3 | 2 |
| N Alternative genotype in Med | | 13 | 14 | 14 | 14 | 15 |
| Freq of the Fav allele | | 0.12 | 0.09 | 0.09 | 0.09 | 0.06 |
| N with genotype in small | | 10 | 10 | 10 | 10 | 10 |
| N REF genotype in small | | 5 | 4 | 4 | 4 | 4 |
| N het genotype in small | | 4 | 5 | 5 | 5 | 6 |
| N Alternative genotype in small | | 1 | 1 | 1 | 1 | 0 |
| Freq of the Fav allele | | 0.7 | 0.65 | 0.65 | 0.65 | 0.7 |

Table 4. Fingerprinting haplotypes of select small seeded and medium seeded individuals from an F2 watermelon population segregating for seed size. The QTL is expected to be within or in the proximity of the marker interval NW0251455-NW0248118. The marker NW0249783 has not been genetically mapped but its location has been confirmed from watermelon genome sequence. The genotype of the small seeded parent was considered as the favorable allele. The occurrence of the favorable alleles (small) in the medium seeded bulk was calculated, as well as the occurrence of the favorable alleles (small) in the small seeded bulk. A low frequency of the favorable alleles in the medium seeded bulk and a moderately high frequency of the favorable alleles in small seeded bulk indicate a likely position of the QTL at these marker positions.

What is claimed is:

1. A watermelon plant comprising in its genome at least one introgressed allele locus that confers a small seed size phenotype, wherein the small seed phenotype is defined as a seed length of about 6 mm and wherein the locus comprises markers NW0251455 (SEQ ID NO: 5) and NW0248118 (SEQ ID NO: 1) on linkage group 2 (LG2) and wherein said plant lacks marker NW0248583 (SEQ ID NO: 4);
or a progeny plant therefrom, wherein said progeny plant comprises the at least one introgressed allele locus that confers the small seed size phenotype.

2. The watermelon plant of claim 1, wherein the locus comprises markers:
NW0251455 (SEQ ID NO: 5) and NW0249783 (SEQ ID NO: 6) on LG2;
NW0249783 (SEQ ID NO: 6) and NW0250500 (SEQ ID NO: 7) on LG2;
NW0250500 (SEQ ID NO: 7) and NW0250854 (SEQ ID NO: 8) on LG2; or
NW0250854 (SEQ ID NO: 8) and NW0248118 (SEQ ID NO: 1) on LG2.

3. A method of obtaining a watermelon plant according to claim 1, the method comprising the step of: (i) detecting in at least one watermelon plant an allele of at least one polymorphic nucleic acid that confers the small seed size phenotype, wherein the polymorphic nucleic acid comprises markers:
NW0251455 (SEQ ID NO: 5) and NW0248118 (SEQ ID NO: 1) on linkage group 2 (LG2) and wherein said polymorphic nucleic acid lacks marker NW0248583 (SEQ ID NO: 4), thereby obtaining a watermelon plant according to claim 1.

4. The method of claim 3, further comprising the step of: (ii) identifying at least one watermelon plant in which the polymorphic nucleic acid that confers the small seed size phenotype has been detected and denoting that the watermelon plant comprises the polymorphic nucleic acid that confers the small seed size phenotype.

5. The method of claim 4, further comprising the step of: (iii) selecting a denoted watermelon plant from a population of plants.

6. The method of claim 3, wherein the polymorphic nucleic acid comprises markers:
NW0251455 (SEQ ID NO: 5) and NW0249783 (SEQ ID NO: 6) on LG2;
NW0249783 (SEQ ID NO: 6) and NW0250500 (SEQ ID NO: 7) on LG2;
NW0250500 (SEQ ID NO: 7) and NW0250854 (SEQ ID NO: 8) on LG2; or
NW0250854 (SEQ ID NO: 8) and NW0248118 (SEQ ID NO: 1) on LG2.

7. The method of claim 3, wherein at least one of said polymorphic nucleic acids comprises markers:
selected from the group on LG2 consisting of NW0248118 (SEQ ID NO: 1); NW0251455 (SEQ ID NO: 5); NW0249783 (SEQ ID NO: 6); NW0250500 (SEQ ID NO: 7); and NW0250854 (SEQ ID NO: 8).

8. A method for producing a watermelon plant according to claim 1, the method comprising:

(i) crossing a first watermelon plant lacking a locus that confers the small seed size phenotype with a second watermelon plant comprising:
  (a) an allele of at least one polymorphic nucleic acid that confers the small seed size phenotype comprising markers NW0251455 (SEQ ID NO: 5) and (SEQ ID NO: 1) on linkage group 2 (LG2), and
  (b) at least one additional polymorphic nucleic acid comprising marker NW0248583 (SEQ ID NO:4) and an allele that confers an average seed length phenotype genetically linked to said additional polymorphic nucleic acid located outside of said region that is not present in said first watermelon plant, to obtain a population of watermelon plants segregating for the polymorphic nucleic acid that confers the small seed size phenotype and said additional polymorphic nucleic acid;
(ii) detecting said polymorphic nucleic acid in at least one watermelon plant from said population of watermelon plants, and
(iii) selecting a watermelon plant comprising said polymorphic nucleic acid comprising markers NW0251455 (SEQ ID NO:5) and NW0248118 (SEQ ID NO:1) that confers the small seed size phenotype that lacks said additional polymorphic locus nucleic acid comprising marker NW0248583 (SEQ ID NO:4), thereby obtaining a watermelon plant according to claim 1.

9. The method of claim 8, wherein the selected watermelon plant exhibits the small seed size phenotype.

10. The method of claim 8, wherein the polymorphic nucleic acid comprises markers:
  NW0251455 (SEQ ID NO: 5) and NW0249783 (SEQ ID NO: 6) on LG2;
  NW0249783 (SEQ ID NO: 6) and NW0250500 (SEQ ID NO: 7) on LG2;
  NW0250500 (SEQ ID NO: 7) and NW0250854 (SEQ ID NO: 8) on LG2; or
  NW0250854 (SEQ ID NO: 8) and NW0248118 (SEQ ID NO: 1) on LG2.

11. A part of the watermelon plant of claim 1, further defined as pollen, an ovule, a leaf, an embryo, a root, a root tip, an anther, a flower, a fruit, a stem, a shoot, a seed, a protoplast, a cell, and a callus, wherein said part comprises the at least one introgressed allele locus that confers the small seed size phenotype.

12. The part of the watermelon plant of claim 11, wherein said part is a seed.

13. A method of watermelon plant breeding, the method comprising
  crossing the watermelon plant according to claim 1 with itself or a second watermelon plant to produce progeny watermelon plants comprising the polymorphic nucleic acid that confers the small seed size phenotype, the polymorphic nucleic acid comprising markers NW0251455 (SEQ ID NO: 5) and NW0248118 (SEQ ID NO: 1) on linkage group 2 (LG2) and lacking marker NW0248583 (SEQ ID NO: 4).

14. The method of claim 13, wherein the polymorphic nucleic acid comprises markers:
  NW0251455 (SEQ ID NO: 5) and NW0249783 (SEQ ID NO: 6) on LG2;
  NW0249783 (SEQ ID NO: 6) and NW0250500 (SEQ ID NO: 7) on LG2;
  NW0250500 (SEQ ID NO: 7) and NW0250854 (SEQ ID NO: 8) on LG2; or
  NW0250854 (SEQ ID NO: 8) and NW0248118 (SEQ ID NO: 1) on LG2.

15. The method of claim 13, wherein at least one of said polymorphic nucleic acid that confers the small seed size phenotype comprises markers:
  (i) selected from the group on LG2 consisting of NW0248118 (SEQ ID NO: 1); NW0251455 (SEQ ID NO: 5); NW0249783 (SEQ ID NO: 6); NW0250500 (SEQ ID NO: 7); and NW0250854 (SEQ ID NO: 8).

16. A method of obtaining a watermelon plant according to claim 1, the method comprising:
  (i) providing a population of watermelon plants;
  (ii) genotyping at least one watermelon plant in the population with respect to at least one polymorphic nucleic acid that confers a small seed phenotype, the polymorphic nucleic acid comprising markers:
    NW0251455 (SEQ ID NO: 5) and NW0248118 (SEQ ID NO:1) on linkage group 2 (LG2) and lacking marker NW0248583 (SEQ ID NO: 4);
  and
  (iii) selecting from the population at least one watermelon plant according to claim 1.

17. The method of claim 16, wherein the polymorphic nucleic acid comprises markers:
  NW0251455 (SEQ ID NO: 5) and NW0249783 (SEQ ID NO: 6) on LG2;
  NW0249783 (SEQ ID NO: 6) and NW0250500 (SEQ ID NO: 7) on LG2;
  NW0250500 (SEQ ID NO: 7) and NW0250854 (SEQ ID NO: 8) on LG2; or
  NW0250854 (SEQ ID NO: 8) and NW0248118 (SEQ ID NO: 1) on LG2.

18. The method of claim 16, wherein at least one of said polymorphic nucleic acid comprises markers:
  selected from the group on LG2 consisting of NW0248118 (SEQ ID NO: 1); NW0251455 (SEQ ID NO: 5); NW0249783 (SEQ ID NO: 6); NW0250500 (SEQ ID NO: 7); and NW0250854 (SEQ ID NO: 8).

* * * * *

```
                        SEQUENCE LISTING

<160> NUMBER OF SEQ ID NOS: 23

<210> SEQ ID NO 1
<211> LENGTH: 121
<212> TYPE: DNA
<213> ORGANISM: Citrullus lanatus

<400> SEQUENCE: 1
atgcacatcc aaccctgtct gaggtgcttg atgaactatt taaatcagcc aaggtcagtt      60
yaacattttt gtagatcatg cttgacctac aagactagtt cctatgtcaa tggaatccaa     120
c                                                                     121

<210> SEQ ID NO 2
<211> LENGTH: 120
<212> TYPE: DNA
<213> ORGANISM: Citrullus lanatus
```

<400> SEQUENCE: 2

```
tggtctaagg gaggagagag agtttgcttg gcgtccccgg aagcttgaga gaaggaactt      60
kgacaaaatt agaacacgag ggaaataaaa atacatttta ctcaatttta aaatttaaaa     120
```

<210> SEQ ID NO 3
<211> LENGTH: 121
<212> TYPE: DNA
<213> ORGANISM: Citrullus lanatus
<220> FEATURE:
<221> NAME/KEY: misc_feature
<222> LOCATION: (121)..(121)
<223> OTHER INFORMATION: n is a, c, g, or t

<400> SEQUENCE: 3

```
actcgtgaat cgggtaaaga gtcatcccca gaagctctct cagcattttc tgctttcatg      60
yttggtgccc tctcgaaatg tattgctaca atcttgacat accctgcaat caggtaaaaa     120
n                                                                     121
```

<210> SEQ ID NO 4
<211> LENGTH: 121
<212> TYPE: DNA
<213> ORGANISM: Citrullus lanatus

<400> SEQUENCE: 4

```
tatgtagtag atacattagt ccagggatgt aatgtaccta ggcgagactt tactaattcc      60
rgtgcggcca acagatgaca acggggaacc aggagatggt gaatcactat taggtgaagt     120
t                                                                     121
```

<210> SEQ ID NO 5
<211> LENGTH: 120
<212> TYPE: DNA
<213> ORGANISM: Citrullus lanatus
<220> FEATURE:
<221> NAME/KEY: misc_feature
<222> LOCATION: (94)..(95)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t

<400> SEQUENCE: 5

```
tgagataaga tgggatgatc acgggatgac tcagcttttg ttcaaagctt ccacctattt      60
kctattctat tttccttaat ttgtttaaaa aatnnctcnt ctatattttc gaaaattaca     120
```

<210> SEQ ID NO 6
<211> LENGTH: 121
<212> TYPE: DNA
<213> ORGANISM: Citrullus lanatus

<400> SEQUENCE: 6

```
taataatagt tggttaattt gatgagttat atatatatgt gcattacctt tgtcaatgta      60
yagtaactct ctttgaaggc gtttgaactc ttctgaatca attgtaacaa aagttgcaaa     120
g                                                                     121
```

<210> SEQ ID NO 7
<211> LENGTH: 121
<212> TYPE: DNA
<213> ORGANISM: Citrullus lanatus

<400> SEQUENCE: 7

```
tgctttgtgg tgttgcaggt aacttctgtt gaggagacta agaggatgg gggattcttg      60 racagattag aagaagctca agaagcaata agagaagctg atattatgtt aaatgcattg    120
t                                                                    121
```

<210> SEQ ID NO 8
<211> LENGTH: 121
<212> TYPE: DNA
<213> ORGANISM: Citrullus lanatus
<220> FEATURE:
<221> NAME/KEY: misc_feature
<222> LOCATION: (40)..(40)
<223> OTHER INFORMATION: n is a, c, g, or t

<400> SEQUENCE: 8

```
gtaattgtat gccttgtttg aatatagaag aacttttcn gattctgtgt cgaatccatc      60
rtgggggagg aaccctgttg gattggtgta acatgatcca ctccaatctc cttgatttcc    120
t                                                                    121
```

<210> SEQ ID NO 9
<211> LENGTH: 121
<212> TYPE: DNA
<213> ORGANISM: Citrullus lanatus
<220> FEATURE:
<221> NAME/KEY: misc_feature
<222> LOCATION: (96)..(98)
<223> OTHER INFORMATION: n is a, c, g, or t

<400> SEQUENCE: 9

```
gctgcggagt cccaaagagg tgacggagga agagtataca aaattctacc actctcttgc      60
waaggtaatt gtccaaaatg caagcagtga aaaaannnta tatgaaagca ccttaagctg    120
t                                                                    121
```

<210> SEQ ID NO 10
<211> LENGTH: 121
<212> TYPE: DNA
<213> ORGANISM: Citrullus lanatus
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 10

```
ccagctgtta tggttggaag aataaattca gtgagtagac ttcagttctc ctccatgtat      60
wcaagtgttt cggaaccttg ggggtgtggt ggtatttnaa ntaagtaatg tttcctctca    120
g                                                                    121
```

<210> SEQ ID NO 11
<211> LENGTH: 121
<212> TYPE: DNA
<213> ORGANISM: Citrullus lanatus
<220> FEATURE:
<221> NAME/KEY: misc_feature
<222> LOCATION: (39)..(39)
<223> OTHER INFORMATION: n is a, c, g, or t

<400> SEQUENCE: 11

```
cctctgccgc cgccgcctcg tctctccgac caccaaaanc agcttccagt tatgaccatc      60
```

```
rtcctaattc tgttcgtcgc cttttctctc gcttttagtt tctacatcat cgttgtaaaa    120
t                                                                    121

<210> SEQ ID NO 12
<211> LENGTH: 92
<212> TYPE: DNA
<213> ORGANISM: Citrullus lanatus

<400> SEQUENCE: 12
gtaccaatat accttggaca ggaagacatt ggaataaact gaccacccaa ttcaagctct    60
scaacagtgc ccttccactc tttaactaga cc                                  92

<210> SEQ ID NO 13
<211> LENGTH: 121
<212> TYPE: DNA
<213> ORGANISM: Citrullus lanatus
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 13
ttggtttaga tttgtttaga aggaaggtat tgggtaggaa taataattng gggtttngga    60
wtgacagaca gacaaggcat caatgctgga tgagatcata gactatgtaa agtttctcca   120
g                                                                    121

<210> SEQ ID NO 14
<211> LENGTH: 121
<212> TYPE: DNA
<213> ORGANISM: Citrullus lanatus

<400> SEQUENCE: 14
ggcaacccta acaagtggtt tacaatgatc gataatgtat atctttatgt atgttgttca    60
ygatggccca ttctggacaa tttaacaata gatgttagtt caactggcat gatggtcata   120
a                                                                    121

<210> SEQ ID NO 15
<211> LENGTH: 121
<212> TYPE: DNA
<213> ORGANISM: Citrullus lanatus

<400> SEQUENCE: 15
acagacaacc ccatagcttc ctttcccgat tacttcctga attttgtatc tactcgcatc    60
kccataatca gaaaagaact ccacttcggt tgaattctgt tgcataaact gatttagata   120
a                                                                    121

<210> SEQ ID NO 16
<211> LENGTH: 121
<212> TYPE: DNA
<213> ORGANISM: Citrullus lanatus

<400> SEQUENCE: 16
taaaccttca cccaagtgca atttctccat ctctttggca tttagaaatg gcttctggtt    60
kggagtcctc tccttcgaag aaggtttatc tccatcaact ttgagaaaat gatcggacaa   120
g                                                                    121
```

<210> SEQ ID NO 17
<211> LENGTH: 81
<212> TYPE: DNA
<213> ORGANISM: Citrullus lanatus

<400> SEQUENCE: 17
gctatccgtc ctgagttccg rccgccgccg atcttcccaa acggggtcat tgatgacaac    60
cctttgaagc tgctactgcc a                                              81

<210> SEQ ID NO 18
<211> LENGTH: 121
<212> TYPE: DNA
<213> ORGANISM: Citrullus lanatus

<400> SEQUENCE: 18 tcatttctc tctttcaaga gttgagctaa ttacagaacc caattctgga ttagatgacg     60
rgtggaatgc agccacagca gctggacaag cagcaccaca gaagctacct gttagaaggc   120
a                                                                   121

<210> SEQ ID NO 19
<211> LENGTH: 121
<212> TYPE: DNA
<213> ORGANISM: Citrullus lanatus
<220> FEATURE:
<221> NAME/KEY: misc_feature
<222> LOCATION: (91)..(91)
<223> OTHER INFORMATION: n is a, c, g, or t

<400> SEQUENCE: 19
gtgtctcaag tcgtcgactc aataagccta ccattttgga gacttgacca aatagggagc    60
rggtcttgaa caatgggctt caccctctca ntagctcaag agagacttag tttgtggttg   120
a                                                                   121

<210> SEQ ID NO 20
<211> LENGTH: 121
<212> TYPE: DNA
<213> ORGANISM: Citrullus lanatus
<220> FEATURE:
<221> NAME/KEY: misc_feature
<222> LOCATION: (53)..(53)
<223> OTHER INFORMATION: n is a, c, g, or t

<400> SEQUENCE: 20
cgatcctaat cttgagctaa ctatgaagtc ctgtttgttt gaaattatct ttnaatcctg    60
mtgagagtgg tccgagtttg ccaacttaat aactcccatt ttagggataa gaccaagcaa   120
a                                                                   121

<210> SEQ ID NO 21
<211> LENGTH: 120
<212> TYPE: DNA
<213> ORGANISM: Citrullus lanatus

<400> SEQUENCE: 21
gcaattgcag atatgatgcc tgatcatgac aaatggtcaa ttgatattcc ctggtctatc    60
mataagtaaa cattctctga ggggacctaa atctaaagat aacaacctgt ttgaccttct   120

<210> SEQ ID NO 22
<211> LENGTH: 121
<212> TYPE: DNA

```
<213> ORGANISM: Citrullus lanatus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t

<400> SEQUENCE: 22
aacnttaaaa aaaanngttn gatgacatga cactnggatc aattcgtgca tgacatggcg      60
sttagatcaa tttgtgcata taatttgaat gctaccatca aaccctttag cttccgcctc    120
t                                                                    121

<210> SEQ ID NO 23
<211> LENGTH: 121
<212> TYPE: DNA
<213> ORGANISM: Citrullus lanatus

<400> SEQUENCE: 23
tgggcaagct tttttgtgca ccttgactaa tctcacggga caacctgtct gacccttaaa     60
yatttgggtg tcaaggaaac tcgtaggaaa ttaattccta ggtaggtggc caccatggat    120
t                                                                    121
```